(12) United States Patent
Spaete et al.

(10) Patent No.: US 7,589,071 B1
(45) Date of Patent: Sep. 15, 2009

(54) LARGE CAPACITY VIRAL AMPLICON USING A MINIMAL ORILYT FROM HUMAN CYTOMEGALOVIRUS

(75) Inventors: Richard R. Spaete, Emerald Hills, CA (US); George Kemble, Saratoga, CA (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 10/178,049

(22) Filed: Jun. 19, 2002

Related U.S. Application Data

(60) Provisional application No. 60/299,814, filed on Jun. 20, 2001, provisional application No. 60/372,133, filed on Apr. 12, 2002.

(51) Int. Cl.
*A61K 9/12* (2006.01)
*A01N 63/00* (2006.01)
*A01N 65/00* (2009.01)
*A61K 48/00* (2006.01)
*C12N 15/00* (2006.01)

(52) U.S. Cl. ............ 514/44; 424/93.1; 424/93.21; 435/320.1

(58) Field of Classification Search .......... 536/23.1, 536/23.5, 24.1, 24.5; 514/44; 424/93.1; 435/320.1, 455, 468, 471; 800/21, 278
See application file for complete search history.

(56) References Cited

U.S. PATENT DOCUMENTS

| 5,561,063 A * | 10/1996 | Hock et al. ............ 435/320.1 |
| 5,830,727 A * | 11/1998 | Wang et al. ............. 435/457 |
| 6,524,851 B1 * | 2/2003 | Ellis ..................... 435/325 |

FOREIGN PATENT DOCUMENTS

WO    WO 9906582 A1 * 2/1999

OTHER PUBLICATIONS

Deonarain (1998) Expert Opin. Ther. Pat., 8: 53-69.*
Verma (1997) Nature, 389: 239-42.*
Eck, et al., (1996) Goodman & Gilman's The Pharmacological Basis of Therapeutics, McGraw-Hill, New York, NY., pp. 77-101.*
Gorecki (2001) Expert Opin. Emerging Drugs, 6(2): 187-98.*
Takekoshi, et al. (1991) Gene, 101: 209-13.*
van den Pol, et al. (1999) 19(24): 10948-65.*
Persons, et al. (2003) Curr. Hematol. Rep., 2: 348-55.*
Lori, et al. (2002) Am. J. Pharmacogenomics, 2(4): 245-52.*
Romano, et al. (1999) J. Cell. Biochem., 75(3): 357-68.*
Schroeder, et al. (2000) EMBO J., 19(1): 1-9.*
Kemble, et al. (1996) J. Virol., 70(3): 2044-48.*
Masse, et al. (1992) Proc. Natl. Acad. Sci., USA, 89: 5246-50.*
Hahn, et al. (1998): Proc. Natl. Acad. Sci., USA, 95: 3937-42.*
Borst, et al. (2003) Human Gene Therapy, 14: 959-70.*
Slobedman, et al. (2002) Blood, 100(8): 2867-73.*
Mahmood, et al. (2005) Genetic Vaccines and Therapy, 3: 1-11.*
Douglas et al. (2001) "Efficient Human Immunodeficiency virus-based vector transduction of unstimulated human mobilized peripheral blood CD34+ cells in the SCID-hu Thy/Liv model of human T cells lymphopoiesis." *Human Gene Therapy* 12:401-413.
Fraefel et al. (1996) "Helper virus-free transfer of HSV-1 plasmid vectors into neural cells." *Journal of Virology* 70(10): 7190-7197.
Mahmood et al. (1999) "The role of HSV amplicon vectors in cancer gene therapy." *Gene Therapy and Molecular Biology* 4:209-219.
Ramirez et al. (1979) "Defective virions of human cytomegalovirus." *Virology* 96:311-314.
Romi et al. (1999) "Tamplicon-7, a novel T-lymphotropic vector derived from human herpesvirus 7." *Journal of Virology* 73(8):7001-7007.
Spaete and Frenkel (1982) "The herpes simplex virus amplicon: A new eucaryotic defective-virus cloning-amplifying vector." *Cell* 30:295-304.
Spaete and Mocarski (1985) "The a sequence of the Cytomegalovirus genome functions as a cleavage/packaging signal for Herpes Simplex Virus defective genomes." *Journal of Virology* 54(3):817-824.
Stinski et al. (1979) "DNA of human cytomegalovirus: size heterogeneity and defectiveness resulting from serial undiluted passage." *Journal of Virology* 31(1):231-239.
Sun et al. (1999) "Improved titers for helper virus-free herpes simplex virus type 1 plasmid vectors by optimization of the packaging protocol and addition of noninfectious herpes simplex virus-related particles (previral DNA replication enveloped particles) to the packaging procedure." *Human Gene Therapy* 10:2005-2011.
Wang and Vos (1996) "A hybrid herpesvirus infectious vector based on Epstein-Barr virus and herpes simplex virus type 1 for gene transfer into human cells in vitro and in vivo." *Journal of Virology* 70(12):8422-8430.
Wang et al. (1998) "Immune modulation of human B lymphocytes by gene transfer with recombinant Epstein-Barr virus amplicons." *Journal of Virological Methods* 72:81-93.
Chee et al., Analysis of the Protein-Coding Content of the Sequence of Human Cytomegalovirus Strain AD169, 1990, Curr Top Microbiol Immunol. 154, 125-169.
Cha et al., Human Cytomegalovirus Clinical Isolates Carry at Least 19 Genes Not Found In Laboratory Strains, 1996, J Virol 70:78-83.
Mocarski et al., A Deletion Mutant in the Human Cytomegalovirus Gene Encoding IE1-491aa is Replication Defective Due to a Failure in Autoregulation, 1996, PNAS 93:11321-11326.

(Continued)

*Primary Examiner*—Robert M Kelly

(57) ABSTRACT

A novel Human Cytomegalovirus vector system is provided. The vector system is characterized by an amplicon vector, having an HCMV derived origin and cleavage packaging signal, and a helper virus function. The vector system is capable of infecting a wide range of host cells, including human CD34+ hematopoietic progenitor cells. Methods, including therapeutic and prophylactic methods, for introducing heterologous polynucleotide sequences into cells using the vector system are also provided.

24 Claims, 6 Drawing Sheets

OTHER PUBLICATIONS

Cihlar et al., Characterization of Drug Resistance-Associated Mutations in the Human Cytomegalovirus DNA Polymerase Gene by Using Recombinant Mutant Viruses Generated from Overlapping DNA Fragments, 1998, J Virol 72:5927-36.

Haberland et al., Variation Within the Glycoprotein B Gene of Human Cytomegalovirus is Due to Homologous Recombination, 1999, J Gen Virol 80:1495-1500.

Sinzger, C., et al. "Modification of Human Cytomegalovirus Tropism through Propagation in Vitro is Associated . . . " J.Gen.Virol. (1999) 80: 2867-77.

Tugizov, S., et al. "Role of Apical and Basolateral Membranes in Replication of Human Cytomegalovirus . . . " J.Gen.Virol. (1996) 77: 61-74.

* cited by examiner

LARGE CAPACITY VIRAL AMPLICON USING A MINIMAL ORILYT FROM HUMAN CYTOMEGALOVIRUS

CROSS-REFERENCES TO RELATED APPLICATIONS

This application claims priority to and benefit of U.S. Provisional Patent Application Ser. Nos. 60/299,814, filed on Jun. 20, 2001, and 60/372,133, filed on Apr. 12, 2002, the disclosures of each of which is incorporated herein in their entirety for all purposes.

BACKGROUND OF THE INVENTION

HCMV is a member of the betaherpesvirus family (Mocarski (1996) *Cytomegaloviruses and Their Replication* Third ed., vol. 2. Lippincott—Raven Publishers, Philadelphia; Roizman (1996) *Herpesviridae* Third ed., vol. 2. Lippincott—Raven Publishers, Philadelphia). Other members of this family include human herpesvirus 6 (HHV-6), and human herpesvirus 7 (HHV-7), and all are widely distributed in human populations. During productive replication, the 230 kilobase pair (kbp) double stranded DNA viral genome replicates by a rolling circle mechanism, which generates long head-to-tail concatemers that are cleaved to unit length and packaged in capsids. The state of the HCMV genome during latency remains unidentified and is likely to be circular and extrachromosomal (Bolovan-Fritts et al. (1999) *Peripheral blood CD14(+) cells from healthy subjects carry a circular conformation of latent cytomegalovirus genome* Blood 93:394-8). The HCMV genome has been detected in cells within the hematopoietic lineage as early as $CD34^+$ progenitors and up through differentiated macrophages (Hahn et al. (1998) *Cytomegalovirus remains latent in a common precursor of dendritic and myeloid cells* Proc Natl Acad Sci USA 95:3937-42; Kondo et al. (1994) *Human cytomegalovirus latent infection of granulocyte-macrophage progenitors* Proc Natl Acad Sci USA 91:11879-83; Mendelson et al. (1996) *Detection of endogenous human cytomegalovirus in $CD34^+$ bone marrow progenitors* J Gen Virol 77:3099-102; Slobedman & Mocarski (1999) *Quantitative analysis of latent human cytomegalovirus* J Virol 73:4806-12).

Defective HSV viruses created by high multiplicity serial passage of virus stocks have been described on numerous occasions and have been characterized in detail at the molecular level (Cuifo & Hayward (1981) *Tandem repeat defective DNA from the L segment of the HSV genome* Martinus Nijhoff, The Hague; Frenkel et al. (1976) *Anatomy of herpes simplex virus DNA VI. Defective DNA originates from the S component* J Virol 20:527-31; Locker & Frenkel (1979) *Structure and origin of defective genomes contained in serially passaged herpes simplex type 1* J Virol 29:1065-1077; Murray et al. (1975) *Cyclic appearance of defective interfering particles of herpes simplex virus and the concomitant accumulation of early polypeptide VP175*, Intervirology 5:173-84; Schroder et al. (1975) *An unusual defective genotype derived from herpes simplex virus strain ANG* Intervirology 6:270-84; Vlazny & Frenkel (1981) *Replication of herpes simplex virus DNA: localization of replication recognition signals within defective virus genomes* Proc Natl Acad Sci USA 78:742-667). Naturally occurring HSV defective viruses and laboratory derived HSV amplicon vectors are composed of head-to-tail tandem reiterations of subgenomic regions containing a functional origin of DNA replication ($Ori_S$ or $Ori_L$) and a DNA cleavage/packaging signal (Barnett et al. (1983) *Class I defective herpes simplex virus DNA as a molecular cloning vehicle in eucaryotic cells* J Virol 48:384-95; Bear et al. (1984) *Analysis of two potential shuttle vectors containing herpes simplex virus defective DNA* J Mol Appl Genet. 2:471-84; Kwong & Frenkel (1995) *Biology of herpes simplex virus (HSV) defective viruses and development of the amplicon system* Viral Vectors p. 25-42, Academic Press, Inc.; Spaete & Frenkel (1982) *The herpes simplex virus amplicon: A new eucaryotic defective-virus cloning-amplifying vector* Cell 30:295-304; Stow (1982) *Localization of an origin of DNA replication within the TRS/IRS repeated region of the herpes simplex virus type 1 genome* Embo J 1:863-7; Stow & McMonagle (1983) *Characterization of the TRS/IRS origin of DNA replication of herpes simplex virus type 1* Virology 130:427-38; Stow et al. (1983) *Fragments from both termini of the herpes simplex virus type 1 genome contain signals required for the encapsidation of viral DNA* Nucleic Acids Res 11:8205-20). These two cis-acting functions can be relatively small, ranging from about 90-150 base pairs (bp) for the ori and about 250-300 bp for the a sequence.

In contrast to HSV, HCMV does not efficiently produce defective virus genomes. This difference may be related to the distinct biology of the two viruses (Pari & Anders (1993) *Eleven loci encoding trans-acting factors are required for transient complementation of human cytomegalovirus oriLyt-dependent DNA replication* J Virol 67:6979-88). Only two reports have described the identification of what may potentially be HCMV defective viruses created by serial high multiplicity passage (Ramirez et al. (1979) *Defective virions of human cytomegalovirus* Virology 96:311-4; Stinski et al. (1979) *DNA of human cytomegalovirus: size heterogeneity and defectiveness resulting from serial undiluted passage* J Virol 31:231-9). These reports characterized HCMV defectives as very large subgenomic DNA molecules, in some cases extending over two thirds of the genome. The extent of these deletions has made it difficult to predict the minimal genetic complexity required for replication and packaging of an amplicon vector in a CMV infected cell.

The functional HCMV oriLyt is much more complex than either of the HSV oris; the HCMV oriLyt consists of multiple direct and inverted repeats and extends over at least 1500 bp (Anders et al. (1992) *Boundaries and structure of human cytomegalovirus oriLyt, a complex origin for lytic-phase DNA replication* Journal of Virology 66:3373-3384; Anders & Punturieri (1991) *Multicomponent origin of cytomegalovirus lytic-phase DNA replication* J Virol 65:931-937; Hamzeh et al. (1990) *Identification of the lytic origin of DNA replication in human cytomegalovirus by a novel approach utilizing ganciclovir-induced chain termination* J Virol 64:6184-6195; Masse et al. (1992) *Human cytomegalovirus origin of DNA replication (oriLyt) resides within a highly complex repetitive region* Proc Natl Acad Sci USA 89:5246-5250). HCMV is unique among the herpesviruses in not having an origin binding protein homolog that is required for DNA replication (Pari & Anders (1993) *Eleven loci encoding trans-acting factors are required for transient complementation of human cytomegalovirus oriLyt-dependent DNA replication* J Virol 67:6979-88). The HCMV a sequence varies in size from about 550 bp to 762 bp, and includes the conserved pac-1 and pac-2 cis-elements which determine the sites for cleavage of replicated viral DNA (Deiss et al. (1986) *Functional domains within the a sequence involved in the cleavage-packaging of herpes simplex virus DNA* J Virol 59:605-18; Kemble & Mocarski (1989) *A host cell protein binds to a highly conserved sequence element (pac-2) with the cytomegalovirus a sequence* J Virol 63:4715-4728; Spaete & Mocarski (1985) *The a sequence of the cytomegalovirus genome functions as a cleavage/packaging signal for herpes simplex virus defective* genomes *J Virol* 54:817-824; Tamashiro et al. (1984) *Structure of the heterogeneous L-S junction region of human cytomegalovirus strain AD169 DNA J Virol* 52:541-8; Tamashiro & Spector (1986) *Terminal structure and heterogeneity in human cytomegalovirus strain AD169 J Virol* 59:591-604).

The infectivity of CD34+ cells from seropositive and seronegative subjects with HCMV has been tested both in vivo and in vitro (Sindre et al. (1996) *Human cytomegalovirus suppression of and latency in early hematopoietic progenitor cells Blood* 88:4526-33), and HCMV has been shown to infect cells of the hematopoietic lineage (Maciejewski et al. (1992) *Infection of hematopoietic progenitor cells by human cytomegalovirus Blood* 80:170-8; Mendelson et al. (1996) *Detection of endogenous human cytomegalovirus in CD34+ bone marrow progenitors J Gen Virol* 77:3099-102; Mocarski et al. (1993) *Human cytomegalovirus in a SCID-hu mouse: thymic epithelial cells are prominent targets of viral replication Proc Natl Acad Sci USA* 90:104-8; Soderberg et al. (1993) *Definition of a subset of human peripheral blood mononuclear cells that are permissive to human cytomegalovirus infection J Virol* 67:3166-75; Von Laer et al. (1995) *Detection of cytomegalovirus DNA in CD34+ cells from blood and bone marrow Blood* 86:4086-90). Viral genomes can be found in CD34+ cells from seropositive individuals and granulocyte-macrophage progenitors and differentiated macrophages can be infected experimentally (Soderberg et al. (1993) *Definition of a subset of human peripheral blood mononuclear cells that are permissive to human cytomegalovirus infection J Virol* 67:3166-75; Soderberg-Naucler et al. (1997) *Reactivation of latent human cytomegalovirus by allogeneic stimulation of blood cells from healthy donors Cell* 91:119-26). Furthermore, hematopoietic stem cells are also reported as a site for HCMV latency.

While the general feasibility of replication defective viral vectors for other cell types has been shown using other herpesviruses, e.g. HSV, EBV, and HHV-7 (Geller et al. (1997) *Helper virus-free herpes simplex virus-1 plasmid vectors for gene therapy of Parkinson's disease and other neurological disorders Exp Neurol* 144:98-102; Ho (1994) *Amplicon-based herpes simplex virus vectors Methods Cell Biol* 43:191-210; Jacobs et al. (1999) *HSV-1-based vectors for gene therapy of neurological diseases and brain tumors: part II. Vector systems and applications Neoplasia* 1:402-416; Kwong & Frenkel (1995) *Biology of herpes simplex virus (HSV) defective viruses and development of the amplicon system Viral Vectors* p. 25-42, Academic Press, Inc.; Mahmood et al. (1999) *The role of HSV amplicon vectors in cancer gene therapy Gene Therapy and Molecular Biology* 4:209-219; Romi et al. (1999) *Tamplicon-7, a novel T-lymphotrpic vector derived from human herpesvirus 7 J Virol* 73:7001-7007; Wang et al. (1998) *Immune modulation of human B lymphocytes by gene transfer with recombinant Epstein-Barr virus amplicons J Virol Methods* 72:81-93; Wang & Vos (1996) *A hybrid herpesvirus infectious vector based on Epstein-Barr virus and herpes simplex virus type 1 for gene transfer into human cells in vitro and in vivo J Virol* 70:8422-8430), efficient transduction of human CD34+ cells with retroviral and non-viral vectors has been unsatisfactory due to the lack of maintenance of high levels of expression of the transgene following engraftment of the engineered cells (Douglas et al. (2001) *Efficient human immunodeficiency virus-based vector transduction of unstimulated human mobilized peripheral blood CD34+ cells in the SCID- hu Thy/Liv model of human T cell lymphopoiesis Hum Gene Ther* 12:401-13). The approaches to improving the efficiency of gene transfer into human cells have focused on improving gene delivery vectors and optimizing ex vivo culture conditions, which preserve the developmental properties of the stem cells (De Wynter et al. (1999) *Properties of peripheral blood and cord blood stem cells Baillieres Best Pract Res Clin Haematol* 12:1-17; Goerner et al. (2000) *Expansion and transduction of nonenriched human cord blood cells using HS-5 conditioned medium and FLT3-L J Hematother Stem Cell Res* 9:759-65).

The present invention exploits the tropism of HCMV to provide HCMV virus vectors which offer solutions to these and other problems.

SUMMARY OF THE INVENTION

The present invention provides a novel Human Cytomegalovirus (HCMV) derived vector system. In one aspect, the invention provides isolated or recombinant nucleic acids comprising a viral amplicon. The viral amplicon is characterized by an HCMV replication origin (oriLyt) and an HCMV cleavage packaging signal facilitating packaging by a helper virus. In some embodiments, the viral amplicon also includes a promoter for regulating transcription of a heterologous polynucleotide. In some embodiments, the viral amplicon includes a heterologous polynucleotide operably linked to a promoter, such as the HCMV major immediate early (MIE) promoter. The isolate or recombinant nucleic acid can be a vector, such as plasmid. In one preferred embodiment, the vector is the plasmid Tn9-8. The plasmid Tn9-8 was deposited with the American Type Culture Collection (ATCC®, 10801 University Boulevard, Manassas, Va. 20110-2209) on Jun. 5, 2008 and assigned Accession No. PTA-9266. This deposit will be maintained under the terms of the Budapest Treaty on the International Recognition of the Deposit of Microorganisms for the Purposes of Patent Procedure. Since the strain referred to is being maintained under the terms of the Budapest Treaty, it will be made available to a patent office signatory to the Budapest Treaty.

Another aspect of the invention relates to vector systems including a helper-dependent virus vector comprising a viral amplicon, including a HCMV replication origin and cleavage packaging signal, and a helper virus. Optionally, the helper virus is a replication incompetent HCMV. Optionally, the vector system can be supplied as a kit.

Compositions comprising the vectors of the invention in a carrier or excipient, such as a pharmaceutically acceptable carrier or excipient, are another feature of the invention.

Another aspect of the invention relates to methods for introducing a heterologous polynucleotide into cells by contacting cells with an infectious viral stock including the viral amplicons of the invention. The viral stocks can be produced, for example, by culturing cells incorporating the viral amplicon, and expressing a helper virus, and recovering infectious viral stocks from the cultured cells. The helper virus can be a replication competent, packaging competent HCMV strain, e.g., an HCMV Towne strain. Alternatively, the helper virus is replication incompetent. In some embodiments, viral stocks are produced in a helper virus free cell culture system. In some embodiments, the cells are mammalian cells, such as human fibroblasts.

In another aspect, the invention provides methods of increasing hemaglobin production in a cell. The methods involve contacting a hematopoietic stem cell, e.g., a CD34+ stem cell, with an infectious viral stock comprising the viral amplicons of the invention comprising a heterologous polynucleotide encoding a hemaglobin polypeptide operably linked to a promoter active in the hematopoietic stem cell and/or its progeny. The cells are contacted in vitro, in vivo, or ex vivo. In some embodiments, the infected cells expressing the hemaglobin polypeptide are introduced into a mammalian subject. In some embodiments, the subject is a human subject, e.g., with a hematological disorder, such as a hemaglobinopathy. Methods for treating a hematological disorder, such as a hemaglobinopathy, e.g., a genetic hemaglobinopathy such as thalassemia, sickle cell anemia by contacting hematopoietic stem cells with infectious viral stocks including the viral amplicons of the invention capable of expressing heterologous polynucleotides are also a feature of the invention.

In yet another aspect, the invention provides methods of reducing retroviral replication in a cell. The methods involve contacting a cell of the hematopoietic lineage, such as a hematopoietic stem cell, e.g., a CD34$^+$ stem cell, with an infectious viral stock comprising the viral amplicons of the invention comprising a heterologous polynucleotide encoding an anti-retroviral antisense RNA or ribozyme, operably linked to a suitable promoter. In an embodiment, the promoter is the major immediate early (MIE) promoter of HCMV. The cells are contacted in vitro, in vivo, or ex vivo. Expression of the anti-retroviral antisense RNA or ribozyme, e.g., specific for a transcript involved in retroviral replication results in a reduction of retroviral replication in the infected cell. Optionally, the infected cells are introduced into a mammalian subject, such as a human subject, e.g., a human subject with a condition or disease produced by a viral infection, e.g., HIV/AIDS. Methods of treating a condition or disease produced by a viral infection, e.g., a retroviral infection, such as HIV/AIDS, are also a feature of the invention. The methods of the invention for treating a viral condition or disease involve contacting at least one cell of the hematopoietic lineage with an infectious viral stock comprising a viral amplicon of the invention capable of expressing a heterologous polynucleotide encoding an anti-retroviral antisense RNA or ribozyme. Expression of the anti-retroviral antisense RNA or ribozyme in the infected cell results in a reduction in retroviral replication, thereby treating the condition or disease produced by the viral infection.

DETAILED DISCUSSION

Figure 1:
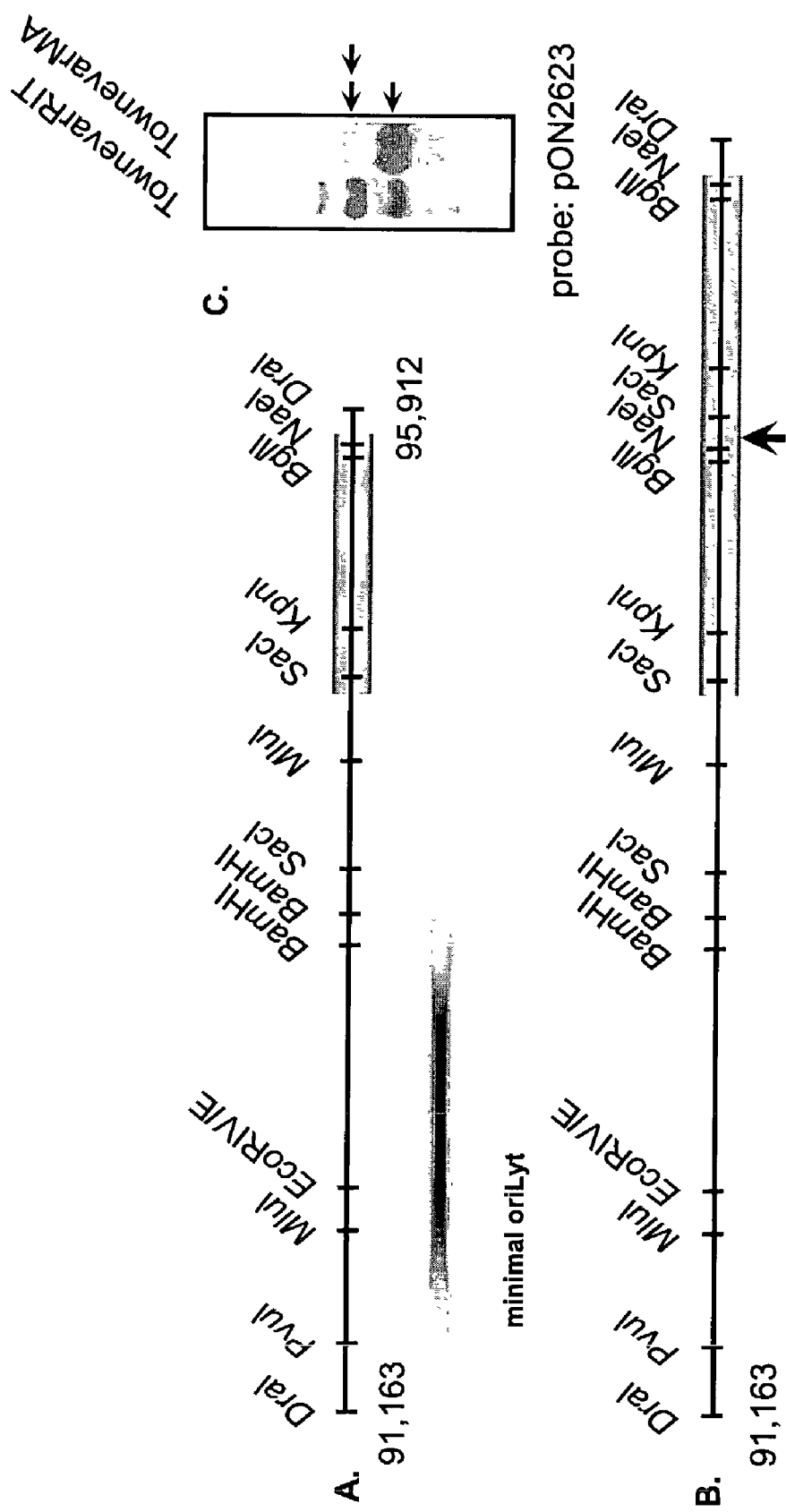
FIG. 1. A. and B. Schematic representation of amplified region near oriLyt of the HCMV genome. C. Southern blot illustrating heterogeneity of oriLyt.

The present invention relates to a helper-dependent virus vector system which is derived from Human Cytomegalovirus (HCMV). The vector is based on the herpes simplex virus (HSV) amplicon system and contains the HCMV orthologs of the two cis-acting functions required for replication and packaging of viral genomes, the complex HCMV viral DNA replication origin (oriLyt), and the cleavage packaging signal (the a sequence). The HCMV vector replicates and is packaged into infectious virion particles in the presence of helper virus. This vector is capable of delivering and expressing foreign genes in infected cells, including stem cells such as bone marrow or blood derived hematopoietic progenitor cells, e.g., human CD34$^+$ cells. Packaged replication defective viral genomes are maintained by serial passage in fibroblasts, or other susceptible host cells, and can be detected through multiple passages of the cells. Such vectors are useful for gene delivery to cells of the hematopoietic and other cell lineages.

Among the advantages of the vector system of the present invention is the ability to efficiently infect and deliver genetic information to dividing and non-dividing cell types which support HCMV infection (see, e.g., Sindre et al. (1996) *Human cytomegalovirus suppression of and latency in early hematopoietic progenitor cells Blood* 88:4526-33), such as cells of the hematopoietic lineage, including stem cells, e.g., CD34$^+$ stem cells (Maciejewski et al. (1992) *Infection of hematopoietic progenitor cells by human cytomegalovirus Blood* 80:170-8; Mendelson et al. (1996) *Detection of endogenous human cytomegalovirus in CD34$^+$ bone marrow progenitors J Gen Virol* 77:3099-102; Mocarski et al. (1993) *Human cytomegalovirus in a SCID-hu mouse: thymic epithelial cells are prominent targets of viral replication Proc Natl Acad Sci USA* 90:104-8; Soderberg et al. (1993) *Definition of a subset of human peripheral blood mononuclear cells that are permissive to human cytomegalovirus infection J Virol* 67:3166-75; Von Laer et al. (1995) *Detection of cytomegalovirus DNA in CD34$^+$ cells from blood and bone marrow Blood* 86:4086-90). The HCMV vectors of the invention introduce isolated or heterologous nucleic acids into a cell without inducing the cytopathology characteristically associated with HSV amplicon vector systems, making these vectors more suitable for therapeutic and/or prophylactic applications. For example, genetic hematological disorders such as thalassemias, sickle-cell anemia, and other hemaglobinopathies can be targeted for therapy with this strategy. Another advantage of the system is that vector DNA can be maintained as an episome with minimal concern for the potential consequences of random integration of vector DNA, such as activation of oncogenes or inactivation of tumor suppressor or other essential genes. While HCMV genomes are typically carried continuously in cells of hematopoietic origin in infected individuals, if desired, in order to insure efficient segregation as an episome, the EBV latent replication origin, oriP, and the transactivator, EBNA-1, can be added, as has been done previously with another hybrid herpesvirus vector (Wang & Vos (1996) *A hybrid herpesvirus infectious vector based on Epstein-Barr virus and herpes simplex virus type 1 for gene transfer into human cells in vitro and in vivo J Virol* 70:8422-8430). Yet another advantage, as with other herpesviral vectors, is that the HCMV vector system has the capacity for very large inserts. For example, the HCMV amplicons of the present invention can accommodate mammalian artificial chromosome segments, such as the satellite DNA-based artificial chromosome (SATAC).

DEFINITIONS

Unless defined otherwise, all scientific and technical terms are understood to have the same meaning as commonly used in the art to which they pertain. For the purpose of the present invention the following terms are defined below.

The terms "nucleic acid," "polynucleotide," "polynucleotide sequence" and "nucleic acid sequence" refer to single-stranded or double-stranded deoxyribonucleotide or ribonucleotide polymers, or chimeras or analogues thereof. As used herein, the term optionally includes analogs of naturally occurring nucleotides (e.g., peptide nucleic acids) having the essential nature of natural nucleotides in that they hybridize to single-stranded nucleic acids in a manner similar to naturally occurring nucleotides. Unless otherwise indicated, a particular nucleic acid sequence of this invention encompasses complementary sequences, in addition to the sequence explicitly indicated.

The term "gene" is used broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence.

Genes also optionally include nonexpressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "Tissue specific" promoter or enhancer is one which regulates transcription in a specific tissue type or cell type, or types.

In the context of the invention, the term "isolated" refers to a biological material, such as a nucleic acid or a protein, which is substantially free from components that normally accompany or interact with it in its naturally occurring environment. The isolated material optionally comprises material not found with the material in its natural environment, e.g., a cell. For example, if the material is in its natural environment, such as a cell, the material has been placed at a location in the cell (e.g., genome or genetic element) not native to a material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids.

The term "recombinant" indicates that the material (e.g., a nucleic acid or protein) has been synthetically (non-naturally) altered by human intervention. The alteration to yield the synthetic material can be performed on the material within or removed from its natural environment or state.

The term "operably linked" when referring to a first and a second nucleic acid, or nucleic acid segment or subsequence, indicates that a functional relationship exists between the two nucleic acids. For example, if a first nucleic acid, e.g., a coding sequence is "operably linked" to a second nucleic acid, e.g., a promoter and/or enhancer, the coding sequence is subject to transcription regulatory control by the promoter and/or enhancer.

The term "introduced" when referring to a heterologous or isolated nucleic acid refers to the transfer of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation" and "transduction."

The term "host cell" means a cell which contains a heterologous nucleic acid, such as a vector, and supports the replication and/or expression of the nucleic acid. Host cells can be prokaryotic cells such as E. coli, or eukaryotic cells such as yeast, insect, amphibian, or mammalian cells, including human cells.

The terms "viral amplicon" or "amplicon vector" or, simply, "amplicon" are used herein to designate a genetic element, e.g., a plasmid, carrying a virus derived origin of replication and packaging site, which can be used as a vector to deliver heterologous nucleic acids, e.g., genes, to a host cell. The unit amplicon vector is replicated and can be packaged as a concatemer into functional virion particles. By definition, amplicons are "helper dependent," that is, they require a helper virus, or its functional equivalent, for packaging into an infectious stock.

A "replication origin" or "origin of replication" is a site in a DNA molecule at which DNA replication is initiated.

A "cleavage packaging signal" is a nucleic acid sequence of a virus, or viral amplicon, which is necessary for packaging the viral nucleic acid or amplicon into an infectious virus particle.

A "helper virus" can be a replication and packaging competent virus capable of packaging replication- or packaging-defective nucleic acids into infectious viral particles. Alternatively, a helper virus can be a replication incompetent virus capable of packaging replication- or packaging-defective nucleic acids into infectious viral particles.

Vector Construction

Viral amplicon based vector systems typically include a recombinant plasmid vector having a viral origin of replication and virus-derived cleavage packaging signals, and a compatible helper virus which supplies trans-acting functions necessary for replication and gene expression. The present invention provides amplicon vectors in which the essential cis-acting functions are derived from a human cytomegalovirus (HCMV) to produce a simple plasmid vector capable of generating full-length viral concatemers upon helper virus mediated replication. The HCMV origin of replication (oriLyt) mediates lytic-phase DNA replication in the intact virus, and, when cloned, can mediate DNA replication in a transient transfection assay. The essential HCMV packaging signals are provided by an evolutionarily conserved polynucleotide sequence designated the a sequence, and derived from the cleavage and packaging signal mapped to the ends and repeat junctions of the HCMV virus.

While the replication origin and packaging signals, e.g., the a sequence, can favorably be derived from any of a variety of HCMV strain and/or isolates at the discretion of the practitioner, for simplicity, the following illustrative embodiment (illustrated in FIG. 2) employs the following components throughout. To facilitate identification of relevant portions of the HCMV genome, nucleotide positions are given with reference to the AD169 strain. The oriLyt is derived from a 6 kbp DraI fragment of the TownevarRIT strain (nts 91,166-95,909 relative to AD169). The a region is derived from an 1800 bp XhoI fragment originally isolated from the L-S junction of the CMV Towne strain (Spaete & Mocarski (1985) *The a sequence of the Cytomegalovirus genomefunctions as a cleavage/packaging signal for Herpes Simplex Virus defective genomes J Virol* 54:817-824; GenBank Accession No. M10063 Version M10063.1; GI:330605). While the vectors described throughout are derived from human CMV, and thus are useful for infecting, and introducing heterologous polynucleotides into, human, and certain non-human primate, e.g., chimpanzee, or gorilla cells, comparable vectors can be produced from other species specific CMV strains, e.g., murine CMV, by substituting the appropriate origin and packaging signal sequences.

A variety of plasmid vectors providing suitable backbones for use in the context of the amplicon vectors of the present invention are available. Exemplary embodiments are constructed by inserting the HCMV oriLyt and a sequences into a pUC (e.g., pUC9) plasmid. However, numerous commercially available plasmids, such as multifunctional E. coli cloning and expression vectors, including e.g., pBR322;

pGEM (Promega, Madison, Wis.); BLUESCRIPT (Stratagene, La Jolla, Calif.); pIN vectors (Van Heeke & Schuster (1989) *J Biol Chem* 264:5503-5509); pET vectors (Novagen, Madison Wis.); and the like, are also suitable. Typically, the vector also includes one or more of the following additional functional sequences: a signal sequence, one or more marker genes, a promoter, an enhancer element, and a transcription termination sequence. Construction of suitable vectors containing the HCMV oriLyt and a sequences, along with one or more of these components employs standard ligation techniques, which are known to the skilled artisan.

Typically, the selectable marker encodes a protein that confers resistance to an antibiotic, such as ampicillin, neomycin, tetracycline, or a toxin, e.g., methotrexate. Alternatively, the selectable marker is capable of complementing an auxotrophic deficiency or supplying a critical nutrient absent from the culture medium. In addition, sequences encoding visible, e.g., fluorescent or fluorogenic, markers, such as green fluorescent protein (GFP) can favorably be employed, and detected through non-selective means, such as flow cytometry.

Optionally, the amplicon vector includes an additional origin of replication to improve stability of episomal replication in the host cell. For example, the Epstein-Barr virus (EBV) OriP (in conjunction with the EBNA1 gene), the SATAC (mammalian satellite DNA) derived origin, or other cellular origins, are suitable supplementary origins of replication in the context of the amplicons of the invention.

Typically, the vector includes one or more cloning site, i.e., unique restriction enzyme recognition sites, to facilitate insertion of heterologous polynucleotide sequences, including, e.g., polynucleotide sequences encoding polypeptides (or peptides) or RNA molecules of interest.

Expression Vectors

The heterologous nucleic acid to be expressed is usually operatively linked to an appropriate transcription control sequence (promoter) to direct mRNA synthesis. In certain instances, HCMV derived promoters are used, e.g., the MIE promoter of HCMV. In other cases, e.g., for regulating conditional expression, other promoters are desirable. Numerous viral and mammalian, e.g., human promoters are available, or can be isolated according to the specific application contemplated. For example, alternative promoters obtained from the genomes of animal and human viruses include such promoters as the adenovirus (such as Adenovirus 2), papilloma virus, hepatitis-B virus, polyoma virus, and Simian Virus 40 (SV40), and various retroviral promoters. Mammalian promoters include, among many others, the actin promoter, hemaglobin promoters, immunoglobulin promoters, heat-shock promoters, and the like.

Transcription of a heterologous DNA inserted into the amplicon vector can often be increased by including an enhancer sequence. Enhancers are typically short, e.g., 10-500 bp, cis-acting DNA elements that act in concert with a promoter to increase transcription. Many enhancer sequences have been isolated from mammalian genes (e.g., hemaglobin, elastase, albumin, alpha-fetoprotein, and insulin), and eukaryotic cell viruses. The enhancer can be spliced into the vector at a position 5' or 3' to the heterologous coding sequence, but is typically inserted at a site 5' to the promoter. Typically, the promoter, and if desired, additional transcription enhancing sequences are chosen to optimize expression in the host cell type into which the heterologous DNA is to be introduced. Optionally, the amplicon can also contain a ribosome binding site or an internal ribosome entry site (IRES) for translation initiation.

The amplicon vectors of the invention also favorably include sequences necessary for the termination of transcription and for stabilizing the mRNA. Such sequences are commonly available from the 5' and, occasionally 3', untranslated regions of eukaryotic or viral DNAs or cDNAs. The vector optionally includes appropriate sequences for amplifying expression.

In addition, as described above, the expression vectors optionally include one or more selectable marker genes to provide a phenotypic trait for selection of transformed host cells, in addition to genes previously listed, markers such as dihydrofolate reductase or neomycin resistance are suitable for selection in eukaryotic cell culture.

The vector containing the appropriate DNA sequence as described above, as well as an appropriate promoter or control sequence, can be employed to transform a host cell permitting expression of the protein. While the amplicon vectors of the invention can be replicated in bacterial cells, most frequently it will be desirable to introduce them into mammalian, e.g., human cells for the purpose of expression.

Additional Expression Elements

Specific initiation signals can aid in efficient translation of a heterologous coding sequence of interest. These signals can include, e.g., the ATG initiation codon and adjacent sequences. In cases where the heterologous coding sequence, its initiation codon and upstream sequences are inserted into the appropriate expression vector, no additional translational control signals may be needed. However, in cases where only coding sequence (e.g., a mature protein coding sequence), or a portion thereof, is inserted, exogenous transcriptional control signals including the ATG initiation codon must be provided. Furthermore, the initiation codon must be in the correct reading frame to ensure translation of the entire insert. Exogenous transcriptional elements and initiation codons can be of various origins, both natural and synthetic. The efficiency of expression can be enhanced by the inclusion of enhancers appropriate to the cell system in use (Scharf et al. (1994) *Heat stress promoters and transcription factors Results Probl Cell Differ* 20:125-62; Kriegler et al. (1990) *Assembly of enhancers, promoters, and splice signals to control expression of transferred genes Methods in Enzymol* 185: 512-27).

Where desired, polynucleotide sequences encoding additional expressed elements, such as signal sequences, secretion or localization sequences, and/or the like, can be incorporated into the vector, usually, in-frame with the polynucleotide sequence of interest, e.g., to target polypeptide expression to a desired cellular compartment, membrane, or organelle, or to direct polypeptide secretion to the periplasmic space or into the cell culture media. Such sequences are known to those of skill, and include secretion leader peptides, organelle targeting sequences (e.g., nuclear localization sequences, ER retention signals, mitochondrial transit sequences), membrane localization/anchor sequences (e.g., stop transfer sequences, GPI anchor sequences), and/or the like.

Production of Transformation Competent Viral Stocks

Amplicon Production

Amplicon plasmids can be replicated conveniently in bacterial cells, such as *Escherichia coli*, to produce yields suitable for transformation of mammalian, e.g., human cells, with vector DNA. Manipulation of amplicon plasmids is performed according to standard procedures, e.g., as described in Ausubel et al. *Current Protocols in Molecular Biology* (supplemented through 2002) John Wiley & Sons, New York; Sambrook et al. *Molecular Cloning—A Laboratory Manual* (3nd Ed.), Vol. 1-3, Cold Spring Harbor Laboratory, Cold Spring Harbor, N.Y., 2001, and Berger and Kimmel *Guide to Molecular Cloning Techniques, Methods in Enzymology* volume 152 Academic Press, Inc., San Diego, Calif. Briefly, isolated amplicon DNA is introduced (e.g., transformed) into bacterial host cells using well established procedures, e.g., eletroporation, $CaCl_2$/heat shock, lipofection, etc. Following the transformation procedure, the bacterial cells are incubated in the presence of a selection agent, such as ampicillin (corresponding to a selectable marker incorporated into the amplicon plasmid as described above), and resistant colonies which have acquired the amplicon plasmid are selected. Bacterial cells incorporating the amplicon are then grown, e.g., in liquid cultures, from which the amplicon plasmid can be recovered quantitatively using routine methods for the isolation of plasmid DNA. Traditional methods, e.g., CsCl gradients, PEG precipitation, or the like, can be employed, as can commercially available kits, see, e.g., Qiagen, www.qiagen.com; Mo Bio (UltraClean™), www.mobio.com; Promega (Wizard™), www.promega.com).

Helper Virus

HCMV is capable of infecting a broad range of tissue types including cultured primary and immortalized fibroblasts (e.g., skin derived fibroblasts), smooth muscle cells, endothelial cells, epithelial cells, trophoblast cells, hepatocytes, neural cells, stems cells, and cells of the hematopoietic lineage, including mature macrophages, dendritic cells and granulocyte/macrophage precursors, e.g., $CD34^+$ precursor cells. To establish infected cultures, host cells (selected from the cell types listed above, e.g., skin derived fibroblasts) are infected with intact helper virus, at a multiplicity of infection (m.o.i.) of approximately 1 plaque forming unit (PFU) per cell, or transfected, e.g., by electroporation or calcium phosphate precipitation, with purified viral DNA. Virus is grown in culture until the host cells are well infected, typically, for approximately 6-10 days (e.g., about 7 days). The cultures are refed as necessary to provide adequate growth and metabolic conditions for the infected cells, e.g., approximately every 3-5 days. Typically, propagation of the virus is accomplished under conditions and media compositions in which the host cell is commonly cultured. For example, propagation of helper virus in human fibroblast (HF) cells is readily accomplished by culturing the infected cells in a standard commercial culture medium, such as Dulbecco's modified Eagle's medium supplemented with serum (e.g., 10% fetal bovine serum) at 37° C., under controlled humidity and $CO_2$ concentration suitable for maintaining neutral buffered pH. Optionally, the medium contains antibiotics to prevent bacterial growth, e.g., penicillin, streptomycin, etc., and/or additional nutrients, such as L-glutamine, sodium pyruvate, non-essential amino acids, and the like. Either primary fibroblasts, e.g., foreskin derived fibroblasts or established cell lines, e.g., MRC-5 cells, including immortalized MRC-5-h-tert (Mc-Sharry et al. (2000) *Human telomerase reverse transcriptase-immortalized MRC-5 and HCA2 fibroblasts are fully permissive for human cytomegalovirus J Gen Virol* 82:855-863), and the like, can be employed. Culture conditions suitable for maintaining mammalian cells have been extensively reported, and are known to those of skill in the art. General protocols are provided, e.g., in Freshney (1983) *Culture of Animal Cells: Manual of Basic Technique*, Alan R. Liss, New York; Paul (1975) *Cell and Tissue Culture*, $5^{th}$ ed., Livingston, Edinburgh; Adams (1980) *Laboratory Techniques in Biochemistry and Molecular Biology-Cell Culture for Biochemists*, Work and Burdon (eds.) Elsevier, Amsterdam. Additionally, variations in such procedures adapted to the present invention are readily determined through routine experimentation.

A suitable helper virus is selected from among available HCMV viral stocks at the discretion of the practitioner. For example, HCMV Toledo and HCMV Towne (e.g., Towne-varRIT) are two exemplary helper viruses in the context of the present invention. Additional virus strains are known to those of skill in the art. Alternatively, replication defective helper virus strains can be engineered by deleting the major immediate early (MIE) gene, e.g., IE72, or the a sequence. Such replication defective viruses typically proceed through one round of replication and then abort the infection. In the case of an a sequence deletion, such a non-replicating virus can be propagated in a bacterial artificial chromosome (BAC) and supplied in trans by cotransfection with the amplicon. The IE72 deletion virus can be propagated using complementing cell lines supplying the immediate early gene product or by use of high multiplicity infections. Introduction of helper virus functions through the co-transfection of an overlapping set of cosmids is also contemplated, as described in further detail below in the section entitled "Helper virus free packaging."

If desired, a recombinant virus incorporating one or more detectable markers, e.g., green fluorescent protein, lacZ, or the like, can be utilized to facilitate monitoring of the infection.

Helper virus is then recovered by harvesting the cells in a convenient cell/medium ratio, e.g., by scraping of adherent cells grown in a monolayer, or by centrifugation of cells grown in suspension. The cells are lysed by multiple freeze/thawing (e.g., 3 times) at −80° C., or on dry ice and/or by sonicating (e.g., three times for 10 seconds, on ice, with cooling between each cycle of sonication). Optionally, a sterile 9% w:v solution of powdered milk is added to the medium prior to sonication. The resulting helper virus suspension is then recovered by centrifugation. Stocks are stored in cryovials at −80° C. until use.

Where purified DNA is preferred, the cells can be lysed using a solution of 1.0 M NaCl, 10 mM Tris, 1 mM EDTA, 0.05% SDS, and 0.1 mg/ml Proteinase K (pH8.0). Lysates are incubated approximately 1 hour at 65° C., and extracted once each with an equal volume of phenol, and 1:1 phenol/chloroform. DNA is then precipitated, e.g., using 0.1 volume 3M Sodium Acetate and two volumes ethanol. The viral DNA is then collected (e.g., by spooling onto a glass rod), dried and resuspended into 10 mM Tris, 1 mM EDTA.

Packaging Transformation Competent Viral Stocks

Production of transformation competent viral stocks containing the viral amplicon vector is accomplished by transfecting amplicon DNA, e.g., Tn9-8 amplicon DNA, optionally including a heterologous polynucleotide sequence encoding a polypeptide of interest, into a suitable host cell in culture, such as a human fibroblast cell line, using standard procedures, e.g., Calcium Phosphate precipitation or electroporation. Helper virus is introduced into the cell by superinfection of purified helper virus stocks at high m.o.i. (e.g., an m.o.i. of approximately 5 plaque forming units per cell), or by cotransfection of purified helper virus DNA. The infected host cells are then maintained in culture for approximately 6-7 days, with refeeding of the cells at between days 3 and 5, e.g., on day 4 following infection. Optionally, the transfection derived amplicon containing virion particles are passaged one or more additional times, prior to recovery of infectious stocks. Commonly, in addition to the transfection derived amplicon stock, the population of cells is also supplemented with helper virus to provide replication functions. Helper virus is provided at an m.o.i. between 0.01 and 5 depending on the strain. Optimal m.o.i. for the strain and host cell can be determined empirically by routine experimentation. For example, Towne and Toledo strain helper virus is commonly provided at an m.o.i. of between 1 and 5 for most purposes. MIE deletion strains are typically provided at an m.o.i. of 0.01-1, e.g., to provide amplicon packaging without substantial replication of the helper virus.

Viral stocks containing the packaged amplicon vector are prepared by lysing the host cells (for example by freeze/thawing and/or by sonication as described above with respect to helper virus preparation) and recovering the viral particles, e.g., on sucrose gradients as described, e.g., in Lim et al. (1996) *Packaging defective HSV-1 vectors using an IE-2 deletion mutant supports efficient expression in cultured cortical cell Biotechniques* 7:460-470.

Helper Virus Free Packaging

In some applications, e.g., human prophylactic and/or therapeutic methods, it can be desirable to employ helper virus free vector systems. Such vector systems, which are compatible with the amplicon vectors of the present invention, typically involve the cotransfection of DNA elements comprising a modified viral genome, e.g., lacking the cleavage/packaging site (see, e.g., Fraefel et al (1996) *Helper virus-free transfer of HSV-1 plasmid vectors into neural cells J Virol* 70:7190-7197), or one or more functional MIE gene. The modified viral genome can be supplied in overlapping segments on multiple elements, such as cosmids, (id.), or can be supplied on a single element such as an artificial chromosome, e.g., a BAC (Saiki et al. (1998) *Herpes simplex virus type 1 DNA amplified as bacterial artificial chromosome in Escherichia coli: Rescue of replication-competent viral progeny and packaging of amplicon vectors Hum Gene Ther* 9:2787-2794; Stavropoulos & Strathdee (1998) *An enhanced packaging system for helper-dependent herpes simplex virus J Virol* 72:7137-7143; Horsburgh et al. (1999) *Allele replacement: an application that permits rapid manipulation of herpes simplex virus type 1 genomes Gene Ther* 6:922-930). Titers of transformation competent infectious particles containing amplicon DNA can be improved by supplying previral DNA replication enveloped particles (PREPs) to the cotransfected packaging cells. PREPs are prepared by treating virally infected cells with replication inhibitors such as cytosine-β-D-arabinofuranoside (Ara-C) (Sun et al. (1999) *Improved titers for helper virus-free herpes simplex virus type 1 plasmid vectors by optimization of the packaging protocol and addition of noninfectious herpes simplex virus-related particles (previral DNA replication enveloped particles) to the packaging procedure Hum Gene Ther* 10:2005-2011). Packaging is accomplished in the virus free system by cotransfecting the amplicon vector and modified viral genome elements (e.g., cosmids or BAC) into host cells, which are, optionally, infected with PREPs (e.g., at approximately 1-5 μg/$10^5$-$10^6$ cells). Transformation competent particles are then recovered as described above.

Infection of Cells with the HCMV Amplicon Vector

The amplicon vectors of the invention are useful for introducing and expressing heterologous polynucleotide sequences in a CMV susceptible host cell. A wide variety of heterologous polynucleotides can be introduced into cells using the vectors described herein, including polynucleotides encoding polypeptides (and/or peptides) and/or RNAs, such as antisense RNA molecules or ribozymes. For example, polynucleotides encoding polypeptides such as telomerases can be introduced, using the vectors of the invention, to immortalize primary cells. Similarly, polynucleotides encoding a variety of cytokines, growth factors, antibodies and other bioactive polypeptides and peptides can be introduced into a broad range of cells, including fibroblasts, smooth muscle cells, endothelial cells, epithelial cells, trophoblast cells, hepatocytes, neural cells, stem cells and cells of the hematopoietic lineage, including mature macrophages, dendritic cells and granulocyte/macrophage precursors, e.g., $CD34^+$ precursor cells. Alternatively, polynucleotides encoding antiviral (e.g., anti-retroviral) RNA elements, for example, secondary or tertiary structural RNA competitors effective against viral or cellular factors, e.g., targeting tat-tar and/or RRE-rev interactions, and the like. The CMV amplicon vectors are capable of accommodating and inducing efficient expression of heterologous polynucleotides that extend over a broad size range, from less than 1 kbp to up to approximately 200 kbp (e.g., including mammalian artificial chromosome segments).

Transfection derived viral stocks containing concatemeric amplicon vector DNA are used to infect susceptible host cells, (including a broad range of human cell types) by contacting a population of host cells with amplicon stocks as described above with respect to propagation of helper virus. A population of the selected cells is contacted with packaged amplicon vector comprising a heterologous polynucleotide at a multiplicity of infection (m.o.i.) estimated to effect infection of a high proportion of the cells. Typically an m.o.i. of between about 2 and 10 is employed (e.g., an m.o.i. of between 3 and 7, e.g., an m.o.i. of approximately 4-6, such as an m.o.i of approximately 5). An m.o.i. of 5 is calculated to insure that greater than 99% of the target cells receive at least one infectious amplicon particle, with more than 96% of the cells receiving more than one viral particle. The m.o.i. can be adjusted experimentally to optimize expression of the heterologous polypeptide as desired for a particular application. For example, in therapeutic applications, the m.o.i. is usually calculated to insure that a sufficient amount of the heterologous polypeptide is produced to achieve the desired therapeutic or prophylactic effect.

Therapeutic and Prophylactic Methods and Compositions

The vectors of the invention can be employed to introduce heterologous nucleic acids into a host cell, such as a mammalian cell, e.g., cells derived from a human subject, in combination with a suitable pharmaceutical carrier. The heterologous polynucleotide sequence can encode a polypeptide or peptide, or an RNA such as an antisense RNA or ribozyme. Such compositions contain a sufficient amount of the vector to effect introduction of the vector into one or more host cells, in carrier or excipient, e.g., a pharmaceutically acceptable carrier or excipient. Such a carrier, or excipient, includes, but is not limited to, saline, buffered saline, dextrose, water, glycerol, ethanol, and combinations thereof. The formulation is selected to suit the particular application, e.g., in vitro, in vivo, ex vivo.

For example, one or more members of a population of cells of interest, such as an established cell line, or a sample of cells obtained from a subject (e.g., primary fibroblasts, immortalized fibroblasts, smooth muscle cells, endothelial cells, epithelial cells, trophoblast cells, hepatocytes, neural cells, stem cells, and cells of the hematopoietic lineage, including mature macrophages, dendritic cells and granulocyte/macrophage precursors, e.g., $CD34^+$ precursor cells) are contacted with packaged amplicon-containing virus particles. Optionally, the cells are then returned or delivered to the subject, typically to the site from which they were obtained. In some applications, the cells are grafted onto a tissue, organ, or system site (as described above) of interest, using established cell transfer or grafting procedures. For example, stem cells of the hematopoietic lineage, such as bone marrow, cord blood, or peripheral blood derived hematopoietic stem cells can be delivered to a subject using standard, e.g., intravenous, delivery or transfusion techniques.

Alternatively, the packaged amplicon-containing virus particles can be delivered to the cells of a subject in vivo. Typically, such methods involve the administration of vector particles to a target cell population (e.g., blood cells, skin cells, liver cells, neural (including brain) cells, kidney cells, uterine cells, muscle cells, intestinal cells, cervical cells, vaginal cells, prostate cells, etc., as well as tumor cells derived from a variety of cells, tissues and/or organs. Administration can be either systemic, e.g., by intravenous administration of viral particles, or by delivering the viral particles directly to a site or sites of interest by a variety of methods, including injection (e.g., using a needle or syringe), needleless vaccine delivery, topical administration, or pushing into a tissue, organ or skin site. For example, the viral vector particles can be delivered by inhalation, orally, intravenously, subcutaneously, subdermally, intradermally, intramuscularly, intraperitoneally, intrathecally, by vaginal or rectal administration, or by placing the viral particles within a cavity or other site of the body, e.g., during surgery.

The above described methods are useful for therapeutically and/or prophylactically treating a disease or disorder by introducing a vector of the invention comprising a heterologous polynucleotide encoding a therapeutically or prophylactically effective polypeptide (or peptide) or RNA (e.g., an antisense RNA or ribozyme) into a population of target cells in vitro, ex vivo or in vivo. Typically, the polynucleotide encoding the polypeptide (or peptide), or RNA, of interest is operably linked to appropriate regulatory sequences as described above in the sections entitled "Expression Vectors" and "Additional Expression Elements." Optionally, more than one heterologous coding sequence is incorporated into a single amplicon vector, e.g., an artificial mammalian chromosome. For example, in addition to a polynucleotide encoding a therapeutically or prophylactically active polypeptide or RNA, the vector can also include additional therapeutic or prophylactic polypeptides, e.g., co-stimulatory molecules, cytokines, antibodies, etc., and/or markers, extended genomic regions, and the like.

The methods and vectors of the present invention can be used to therapeutically or prophylactically treat a wide variety of disorders, including genetic and acquired disorders, e.g., hematological disorders, tumors, immunodeficiencies and related disorders.

For example, the methods and vectors of the invention can be used to treat a variety of hematological and immunological disorders, such as a genetic hematological disorder, e.g., a hemaglobinopathy by administering, in vivo, ex vivo or in vitro, a vector of the invention including a heterologous nucleic acid, such as a polynucleotide encoding one or more hemaglobin polypeptides (optionally, in a composition including a pharmaceutically acceptable excipient) to a subject, including, e.g., a human.

For example, dividing cells, such as stem cells, e.g., hematopoietic stem cells, are isolated from a subject, and contacted with infectious viral stocks including a viral amplicon of the invention, such that the viral amplicon is introduced into at least a sub-portion of the cells. Human hematopoietic stem cells, e.g., CD34$^+$ stem cells can be obtained from umbilical cord blood, bone marrow, and at lower frequency from peripheral blood. Umbilical cord blood is recognized as a rich source of hematopoietic CD34$^+$ stem cells (see, e.g., Luther-Wyrsch et al. (2001) *Stable transduction with lentiviral vectors and amplification of immature hematopoietic progenitors from cord blood of preterm human fetuses Hum Gene Ther* 12:377-89) suitable for infection with HCMV amplicon containing stocks or HCMV-EGFP virus. Bone marrow derived CD34$^+$ cells have also been shown to be infectable in vitro with HCMV (e.g., Maciejewski et al. (1992) *Infection of hematopoietic progenitor cells by human cytomegalovirus Blood* 80:170-8).

The contacted cells are then returned or delivered to the subject using standard and well-known grafting techniques or, e.g., delivered to the blood or lymph system using standard delivery or transfusion techniques, where the encoded polypeptide is expressed in a quantity sufficient to remediate the disorder of interest.

For example, a genetic hemaglobinopathy, e.g., sickle cell anemia or a thalassemia, is treated by contacting hematopoietic stem cells with an amplicon comprising a heterologous polypeptide encoding one or more hemaglobin polypeptides. Conditions or diseases associated with, or produced by, viral infection, e.g., retroviral infections, such as acquired immunodeficiency syndrome, i.e., HIV/AIDS, can be treated by administering a vector comprising an antiviral polynucleotide sequence, e.g., an anti-retroviral antisense or ribozyme encoding nucleic acid, such as a hammerhead ribozyme specific for tat, rev, the 5'-LTR, or the transcript encoding gp120. Optionally, the antisense or ribozyme polynucleotide sequence is inserted in, e.g., a small nucleolar RNA such as the U16 RNA, to target the antisense transcript of ribozyme to the nucleolus (Michienzi et al. (2000) *Ribozyme-mediated inhibition of HIV 1 suggests nucleolar trafficking of HIV-1 RNA. Proc Natl Acad Sci USA* 97:8955-8960). Expression of an antisense RNA or ribozyme specific for viral transcripts involved in retroviral replication results in a reduction in retroviral replication, thereby reducing viral load in the infected cells.

Alternatively, in vivo methods in which one or more cells or a population of cells of interest of the subject are contacted directly or indirectly with infectious virus stocks comprising a viral vector of the invention can be used. For example, the packaged virus can be administered or transferred directly to the cells to be treated or to the tissue site of interest (e.g., blood cells), for example by injecting (e.g., by using a needle and/or syringe) the packaged virus into a vessel of the peripheral or central vasculature.

Kits

To facilitate use of the vectors and vector systems of the invention, any of the vectors, e.g., plasmids, amplicons, etc., and additional components, such as helper virus, buffer, cells, culture medium, useful for packaging and infection of the viral amplicons, e.g., Tn9-8, for experimental or therapeutic purposes, can be packaged in the form of a kit. Typically, the kit contains, in addition to the above components, additional materials which can include, e.g., instructions for performing the methods of the invention.

Manipulation of Viral Nucleic Acids

In the context of the invention, nucleic acids and/or proteins are manipulated according to well known molecular biology techniques. Detailed protocols for numerous such procedures, such as the cloning of viral and other nucleic acids, construction of vectors, e.g., amplicon vectors, etc., are described in, e.g., in Ausubel et al. *Current Protocols in Molecular Biology* (supplemented through 2000) John Wiley & Sons, New York ("Ausubel"); Sambrook et al. *Molecular Cloning—A Laboratory Manual* (2nd Ed.), Vol. 1-3, Cold Spring Harbor Laboratory, Cold Spring Harbor, N.Y., 1989 ("Sambrook"), and Berger and Kimmel *Guide to Molecular Cloning Techniques, Methods in Enzymology* volume 152 Academic Press, Inc., San Diego, Calif. ("Berger").

In addition to the above references, protocols for in vitro amplification techniques, such as the polymerase chain reaction (PCR), the ligase chain reaction (LCR), Qβ-replicase amplification, and other RNA polymerase mediated techniques (e.g., NASBA), useful e.g., for amplifying cDNA probes of the invention, are found in Mullis et al. (1987) U.S. Pat. No. 4,683,202; *PCR Protocols A Guide to Methods and Applications* (Innis et al. eds) Academic Press Inc. San Diego, Calif. (1990) ("Innis"); Arnheim and Levinson (1990) C&EN 36; *The Journal Of NIH Research* (1991) 3:81; Kwoh et al. (1989) *Proc Natl Acad Sci USA* 86, 1173; Guatelli et al. (1990) *Proc Natl Acad Sci USA* 87:1874; Lomell et al. (1989) *J Clin Chem* 35:1826; Landegren et al. (1988) *Science* 241: 1077; Van Brunt (1990) *Biotechnology* 8:291; Wu and Wallace (1989) *Gene* 4: 560; Barringer et al. (1990) *Gene* 89:117, and Sooknanan and Malek (1995) *Biotechnology* 13:563. Additional methods, useful for cloning nucleic acids in the context of the present invention, include Wallace et al. U.S. Pat. No. 5,426,039. Improved methods of amplifying large nucleic acids by PCR are summarized in Cheng et al. (1994) *Nature* 369:684 and the references therein.

Certain polynucleotides of the invention, e.g., oligonucleotides can be synthesized utilizing various solid-phase strategies involving mononucleotide- and/or trinucleotide-based phosphoramidite coupling chemistry. For example, nucleic acid sequences can be synthesized by the sequential addition of activated monomers and/or trimers to an elongating polynucleotide chain. See e.g., Caruthers, M. H. et al. (1992) *Meth Enzymol* 211:3.

In lieu of synthesizing the desired sequences, essentially any nucleic acid can be custom ordered from any of a variety of commercial sources, such as The Midland Certified Reagent Company (mcrc@oligos.com), The Great American Gene Company (www.genco.com), ExpressGen, Inc. (www.expressgen.com), Operon Technologies, Inc. (www.operon.com), and many others.

EXAMPLES

Example 1

Heterogeneity at oriLYT

Sequence heterogeneity was observed in the EcoRI E fragment of Towne that was not present in the Toledo strain HCMV (Kemble et al. (1996) *Defined large-scale alterations of the human cytomegalovirus genome constructed by cotransfection of overlapping cosmids J Virol* 70:2044-8). The EcoRI E region partially spans the complex oriLyt region (see, e.g., Anders et al. (1992) *Boundaries and structure of human cytomegalovirus oriLyt, a complex origin for lytic-phase DNA replication Journal of Virology* 66:3373-3384; Anders & Punturieri (1991) *Multicomponent origin of cytomegalovirus lytic-phase DNA replication J Virol* 65:931-937; Hamzeh et al. (1990) *Identification of the lytic origin of DNA replication in human cytomegalovirus by a novel approach utilizing ganciclovir-induced chain termination J Virol* 64:6184-6195; Masse et al. (1992) *Human cytomegalovirus origin of DNA replication (oriLyt) resides within a highly complex repetitive region Proc Natl Acad Sci USA* 89:5246-5250).

Because Towne strain virus replicates to high titers in cell culture, this heterogeneity in the origin region was incorporated into the amplicon construct. To determine which DNA sequences in the Towne genome preserved the heterogeneity, cosmids Tn47 and Tn9 were subjected to restriction enzyme analysis, and Southern blot analysis using plasmid pON2623 as a minimal cis oriLyt probe. Towne-derived cosmids Tn47 and Tn9 were digested to completion with ClaI and DraI. After electrophoresis through a 0.8% agarose gel, the cosmid DNAs were denatured in 0.2M NaCl/0.6M NaOH, neutralized in 0.6M NaCl/1M Tris pH 7.5 in situ, and the gel was soaked in 20×SSC for 30 minutes. Southern blots were prepared by placing a Hybond-N+ nylon membrane (Amersham Corp.), on the gel and transferring the DNAs to the membrane using the capillary action of paper towels. After blotting overnight in 20×SSC, the membrane was washed in 2×SSC and the DNA was immobilized on the membrane using a UV Crosslinker 1000 (Hoefer Scientific Instruments, San Francisco, Calif.).

DNA was probed with fluorescein-labeled plasmid pON2623. After hybridization and exposure of Kodak X-AR film, the hybridization pattern was analyzed revealing that a DraI digest of cosmid Tn9 preserved the heterogeneity. The origin containing DraI fragment was cloned into pON205 by gel extraction as described above and designated clone Tn9-8. The cloned DNA was sequenced in its entirety across the DraI fragment and compared to AD169 DNA sequence in this region. Sequences from nucleotide 94,561 to 95,807 in the reference laboratory strain, AD169, which has been sequenced in its entirety by Chee and colleagues (EMBL accession number X17403), were repeated in the DraI fragment and gave rise to the heterogeneity observed at this locus in the Towne genome.

This segment repeats a variable number of times in Towne strains from different passage histories. FIG. 1 provides a schematic representation of the amplified region near oriLyt of the HCMV genome. Panel A is a restriction enzyme map of minimal oriLyt and adjacent region of heterogeneity (block). In panel B, the region of heterogeneity is shown as a dimer. The arrow indicates the junction between two repeat segments. The number 91,163 to the left of the restriction map corresponds to the nucleotide position of the AD169 genome (EMBL accession number X17403). The coordinates of a single repeat unit starts at nucleotide 94,561 relative to the AD169 sequence and end at nucleotide 95,807 (Chee et al. (1990) *Analysis of the protein-coding content of the sequence of the human cytomegalovirus strain AD*169, p. 125-169 In J. K. McDougall (ed.) *Current Topics in Microbiology and Immunology* vol. 154. Springer-Verlag, Berlin). Panel C shows an autoradiograph of a Southern blot utilizing a minimal oriLyt probe, pON2623 (Kemble et al. (1996) *Defined large-scale alterations of the human cytomegalovirus genome constructed by cotransfection of overlapping cosmids J Virol* 70:2044-8). Monomers and dimers are depicted with one and two arrows, respectively. In addition, trimers and tetramers were observed in the TownevarRIT viral stock. This heterogeneity differs from the previously described 189 bp repeat region which occurs near the BamHI sites of the Towne strain oriLyt (nt 93337-93525 relative to AD169), (see, e.g., Chen et al. (1999) A 189-*bp repeat region within the human cytomegalovirus replication origin contains a sequence dispensable but irreplaceable with other sequences Virology* 258:240-248; Chen et al. (1996) *Strain-dependent differences in the human cytomegalovirus replication origin Archives of Virology* 141:13-30).

Example 2

Construction of HCMV Amplicons

An HCMV amplicon vector was constructed which incorporated the two cis-acting functions required for the propagation of the replication defective virus genomes in the presence of helper virus. This HCMV amplicon plasmid was derived by inserting the 6 kpb DraI fragment of HCMV Towne (TownevarRIT) strain (corresponding to nts 91,166-95,909 relative to AD169) as described above, spanning the HCMV oriLyt into the EcoRI site of pON205 (Spaete & Mocarski (1985) *J Virol* 54:817-824). Briefly, three µg of Tn9 DNA was digested with 80 units of DraI and 20 units of ClaI and electrophoresed in a preparative 0.8% low-melting-point agarose gel for 920 volt hours in 1×TAE buffer. Tn9 DNA migrating at approximately 6 kilobase pairs (kbp) was excised and the agarose was digested with 1 unit of β-agarase I (New England BioLabs, Beverly, Mass.). The DNA fragment was precipitated with 2 volumes of isopropanol, chilled to −20° C., spun in an Eppendorf centrifuge for 15 minutes, washed with 70% cold ethanol, dried and resuspended in 40 µl TE. The gel extracted fragment was ligated to EcoRI digested pON205 using T4 DNA ligase (New England BioLabs, Beverly, Mass.), and an aliquot of the ligation mixture was used to transform competent *Escherichia coli* TOP 10 (Invitrogen, Carlsbad, Calif.) by electroporation using methods as written in the Pulse Controller Guide published by BioRad (Richmond, Calif.). Plasmid DNA was prepared according to manufacturers specifications (Qiagen, Inc., Chatsworth, Calif.). The resulting amplicon, designated Tn9-8 was partially sequenced by the single-cycle and multicyle dideoxy-nucleotide chain termination method of Sanger et al. (Sanger et al. (1977) *DNA sequencing with chain-terminating inhibitors Proc Natl Acad Sci USA* 74:5463-7), on an ABI 373 automated sequencer (Applied Biosystems, Foster City, Calif.). The oriLyt DNA was sequenced in its entirety on both strands, and all junctions were bridged using oligonucleotide primers synthesized on an ABI 392 synthesizer (Applied Biosystems, Foster City, Calif.). The contiguity and analysis of the sequence was performed with MacDNAsis programs (Hitachi Software, San Bruno, Calif.).

Figure 2:
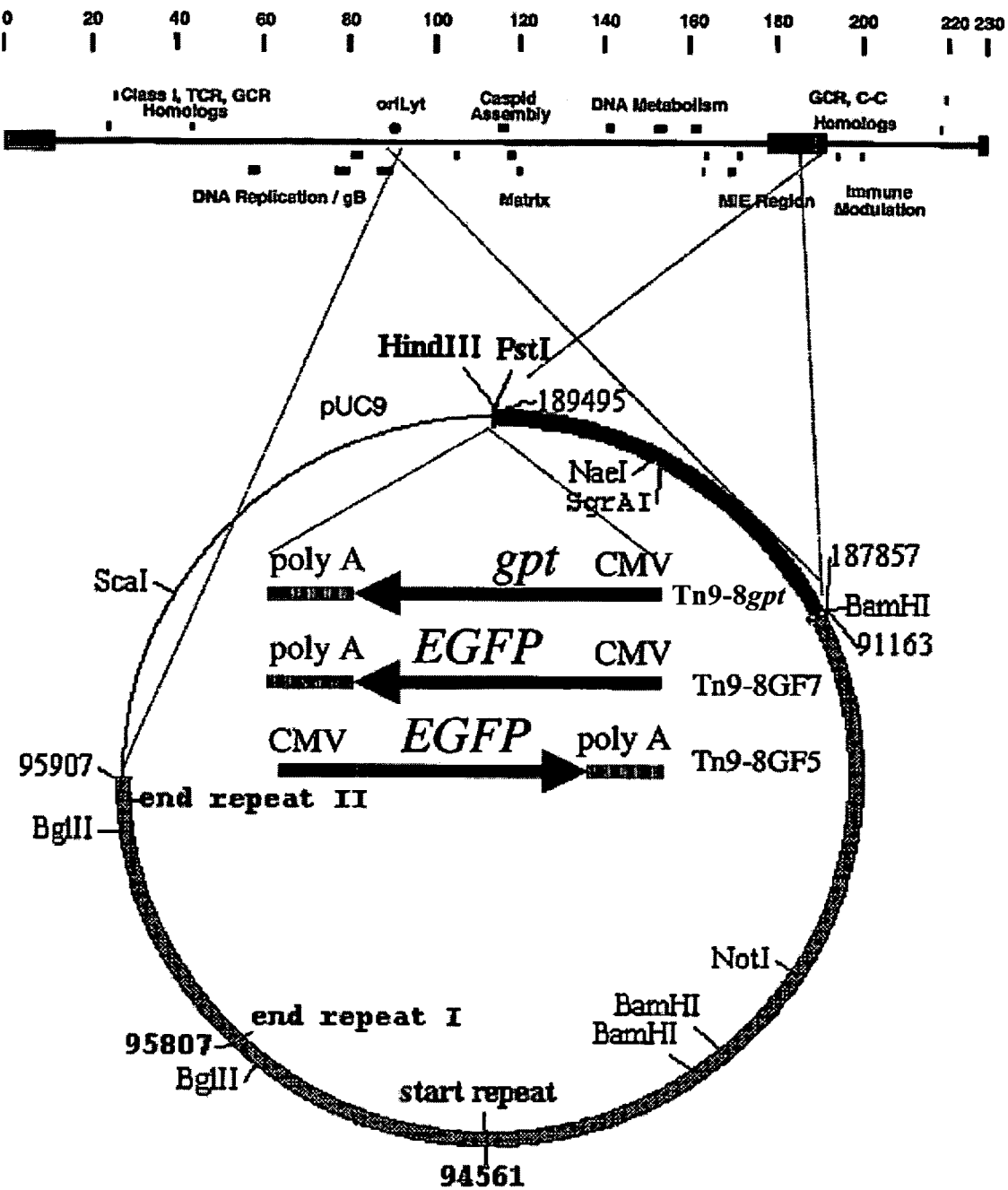
FIG. 2. Schematic representations of the HCMV genome and amplicon vector.

Amplicon plasmid Tn9-8 is illustrated in FIG. 2. The top line, showing unique sequences as a thin line and repeat sequences as black boxes, represents the HCMV genome. Several coding regions are indicated along the linear genome. The location of the lytic origin of replication, oriLyt, and the cleavage/packaging function, the a sequence, used in the construction of the HCMV amplicon (plasmid Tn9-8), are denoted by dashed lines leading to the schematic of the plasmid shown below as a circle. The gpt expression cassette was cloned between the unique PstI and HindIII sites.

The plasmids designated Tn9-8GF5 and Tn9-8GF7, incorporate a 2,334 bp NsiI fragment from plasmid pEGFP-N2 (Clonetech, Palo Alto, Calif.), including the EGFP gene with the HCMV MIE promoter and SV40 poly A sequence, cloned into the HCMV amplicon Tn9-8 at the PstI site in alternative orientations. The gpt gene in Tn9-8-gpt was derived by cloning a PCR fragment from *Escherichia coli* DH5α using the primer pairs 5'CTGCAGCTAGTCTAGACTGGGACACT-TCACATGAGC3' (SEQ ID NO:1), and 5'CTGCAGCTATG-TATCTAGAGCCAGGCGTTGAAAAGATTA3' (SEQ ID NO:2). pEAG2.7EGFP was derived by cloning the EGFP gene from plasmid pEGFP-N2 between the EagI and SmaI site of the β2.7 gene taken from Toledo (G. M. Duke, unpublished data).

Example 3

Generation of Viral Stocks Containing Amplicons

The Tn9-8 plasmid was transfected into human embryonic lung fibroblast (LF) cells using $CaPO_4$ precipitation of approximately 4 µg of amplicon DNA into approximately $1\times10^6$ passage 16 human primary LF cells, and subsequently infected with HCMV Towne strain, which provide helper virus replication.

LF cells from a 225 $cm^2$ flask were split 1:12 and were plated into a 25 $cm^2$ flasks 3 to 5 hours prior to the addition of the DNA-$CaPO_4$ precipitate. The precipitate was adsorbed directly to the cell monolayer for 30 minutes prior to the addition of media. 2 ml of media was added and incubation continued for 3-5 hours at 37° C. in a $CO_2$ incubator. Following the 3-5 hour incubation, the DNA-$CaPO_4$ precipitate was removed, the cells incubated at 37° C. for 3 minutes in 15% glycerol in Hepes buffered saline, rinsed one time with media and fed with 5 ml of media. At 24 hours post transfection, the cells were infected with CMV Towne at a multiplicity of infection (m.o.i.) of 5 plaque forming units (PFU) per cell. Cells were refed at four days post infection.

Figure 3:
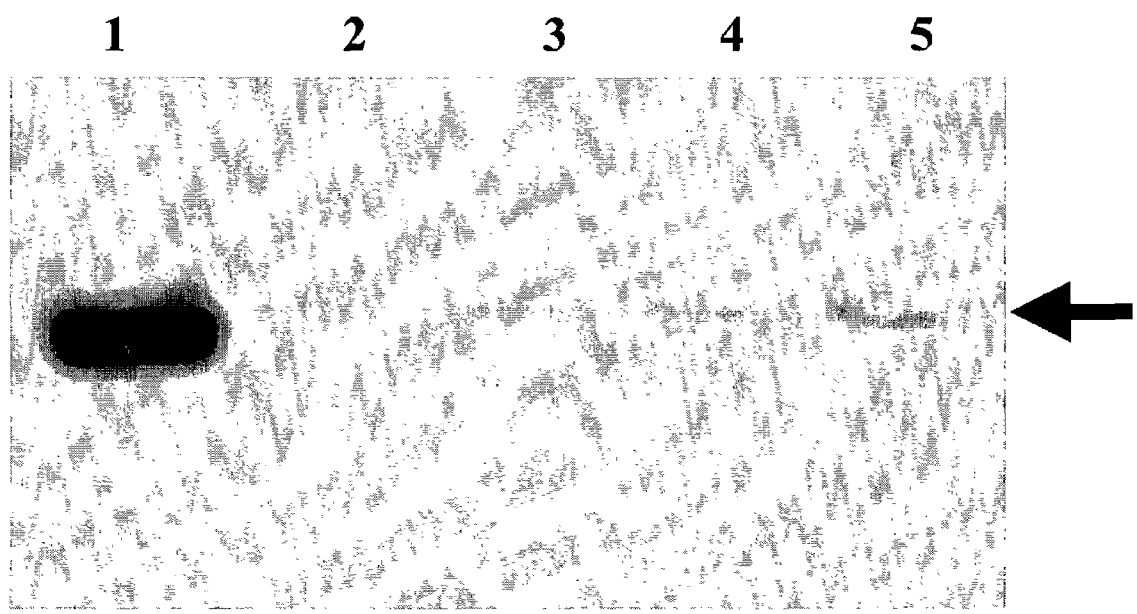
FIG. 3. Southern blot analysis of passage 1 of HCMV amplicon DNA probed with plasmid pUC9.
Figure 4:
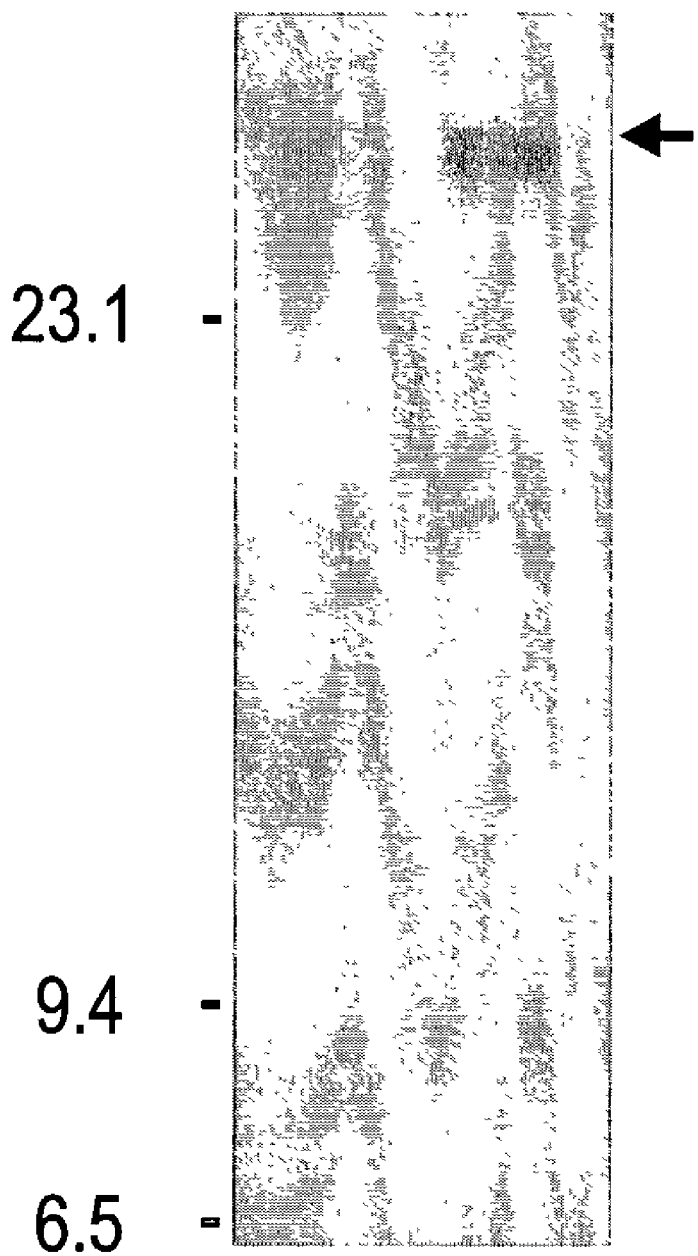
FIG. 4. Southern blot analysis of high molecular weight HCMV amplicon DNA.

Seven days post infection, infected cells were harvested, sonicated, and viral stocks were prepared for passage to fresh LF cells. Fresh LF cells were infected with the progeny of the transfection/infection and incubated for 7 days. The DNA from these infected cells was harvested (designated passage 1), restricted with HindIII and DpnI, and Southern blotted according to established protocols (see, e.g., Maniatis et al.) Southern blot analyses of the DNA, using pUC9 as a probe, demonstrated that Tn9-8 that had not been replicated in a eukaryotic cell was susceptible to digestion with DpnI, consistent with replication of the plasmid in bacteria (FIG. 3). Lane 1, loaded with plasmid Tn9-8 linearized with Hind III serves as a marker for correct migration of monomeric repeats. Lane 2. Plasmid Tn9-8 restricted with Hind III and Dpn I as a control for non-replicating DNA. Lanes 3-5. Infected cell DNAs: Tn9-8 in infected cells was resistant to DpnI digestion demonstrating that it had replicated in eucaryotic cells, consistent with the replication and packaging of Tn9-8 into infectious virions. These results demonstrate that foreign DNA sequences, exemplified by the plasmid pUC9, can be introduced into replication defective genomes that are packaged and propagated in serially passaged virus stocks. To further demonstrate that these results were the consequence of amplicon replication and packaging rather than integration of the amplicon plasmid into the helper virus, DNA prepared from passage 1 infected cells was digested with Cla I, Xba I, Afl II and Dpn I. These enzymes digested the Towne helper virus DNA to fragments no larger than 13.6 kbp but do not cut within Tn9-8. The amplicon DNA was significantly larger than 23 kbp demonstrating that the amplicon replicated as a concatemer. FIG. 4 shows a southern blot analysis of high molecular weight HCMV amplicon DNA at passage 1, probed with plasmid pUC9. DNA prepared from passage 1 infected cells was digested with Cla I, Xba I, Afl II and Dpn I, Southern blotted and probed with plasmid pUC9. The DNA samples are identical to those used in FIG. 3, lanes 3 and 5. The high molecular weight DNA containing plasmid sequences (arrow) demonstrates the major hybridizing species migrating slower than the 23 kbp lambda DNA Hind III digest indicated as the marker on the left of the autoradiograph. This result indicated that the high molecular weight DNA containing plasmid sequences was packaged independently and was not integrated into helper virus. Packaged replication defective viral genomes derived from Tn9-8 or a derivative containing a selectable marker (Tn9-8-gpt), were passaged serially in HF cells. Replication defective viruses could be detected at passage 3 when probed with plasmid pUC9.

Example 4

Rescue of Monomeric Repeat Units in Bacteria

Figure 5:
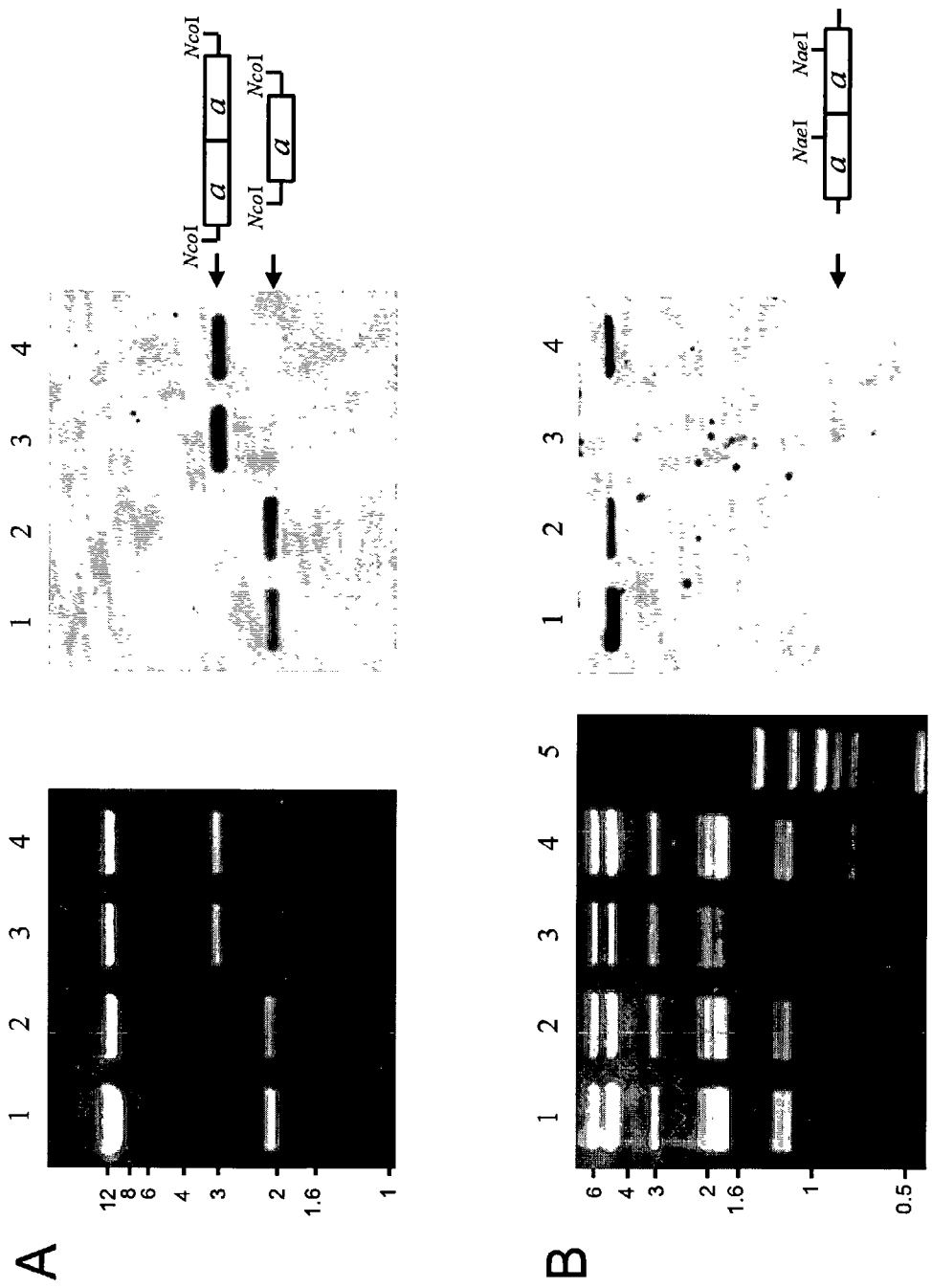
FIG. 5. Southern blot analysis of rescued Tn9-8 concatemers.

Concatemeric DNA was prepared from passage 2 and 3 virus stocks containing the replication defective virus genomes (Tn9-8-gpt), and digested with Pst I and Hind III, respectively, in order to analyze monomeric repeat units. The Hind III digested DNA was circularized by ligation and used to transform *E. coli* bacteria to analyze structure and to demonstrate shuttle vector capability between eucaryotic and bacterial hosts. Following rescue in bacteria, DNA was prepared and cut with NcoI or NaeI as illustrated in FIG. 5. Following restriction enzyme digestion and electrophoresis in 0.8% agarose gels by standard techniques (Maniatis et al., 1982), DNA was transferred to Hybond-N+ nylon membranes (Amersham Corp.). DNA was cross-linked to the membrane with 120,000 microjoules/cm$^2$ of UV irradiation using a UV Crosslinker 1000 (Hoefer Scientific Instruments, San Francisco, Calif.). Hybridizations to immobilized CMV DNA were performed essentially as described by Spaete and Mocarski (1985a), following prehybridization for 1 hour at 68° C. Prehybridization and hybridization were carried out in a solution of 6×SSC (1×SSC is 0.15 M NaCl plus 0.015 M sodium citrate), 0.2% polyvinylpyrrolidone, 0.2% Ficoll, 0.2% bovine serum albumin, and 0.1% sodium dodecyl sulfate, 100 μg/ml salmon sperm DNA and 15% formamide.

Plasmid DNA was labeled in vitro by nick translation (Rigby et al., 1977) with a Southern-Light™ kit (Tropix, Inc., Bedford, Mass.), and using random primed fluorescein-labeled DNA). Fluorescein-labeled probe was denatured by boiling for five minutes, snap-cooled on ice, added to the membrane in 10 mls of hybridization mixture, and allowed to hybridize overnight at 68° C. After hybridization, unannealed probe was removed by rinsing the membrane 3× with 2×SSC followed by reincubation in solution A lacking salmon sperm DNA at 68° C. for 15 minutes. The washing procedure was repeated, the blot was rinsed in a large volume of 2×SSC at room temperature. The membrane was processed according to the membrane blocking and chemiluminescent detection instructions provided by Tropix, Inc. and exposed to Kodak X-AR film.

DNA digested with NcoI is shown in FIG. 5A: ethidium bromide stained agarose gel (left panel); hybridization with the a sequence specific probe (right panel). Lane 1 shows DNA prepared from unpassaged stocks; lane 3 shows DNA prepared from serial passage 2 stocks; and lanes 2 and 4 show DNA prepared from serial passage 3 stocks. A number of plasmids prepared from the rescue attempt had a restriction enzyme pattern indistinguishable from the input. Other plasmids however exhibited the expected restriction pattern consistent with a head-to-tail amplification of the a sequence (lanes 3 and 4).

DNA digested with NaeI is illustrated in FIG. 5B. NaeI digestion produced a fragment of the predicted size of a unit length a sequence (762 bp), and this product hybridized with an a sequence specific probe (PstI-SgrAI fragment from Tn9-8), (FIGS. 2 and 5B, lanes 3 and 4, lane 5 shows a 100 bp ladder).

This type of amplification (i.e., concatemerization of unit repeats) has been observed in restriction enzyme digested DNA preparations of parental genomes of both HSV and HCMV (Locker & Frenkel (1979) *Structure and origin of defective genomes contained in serially passaged herpes simplex type 1 J Virol* 29:1065-1077; Mocarski et al. (1987) *Structure and variability of the a sequence in the genome of human cytomegalovirus (Towne strain) J Gen Virol* 68:2223-30; Mocarski & Roizman (1981) *Site-specific inversion sequence of the herpes simplex virus genome: domain and structural features Proc Natl Acad Sci USA* 78:7047-51; Spaete & Mocarski (1985) *The a sequence of the cytomegalovirus genome functions as a cleavage/packaging signal for herpes simplex virus defective genomes J Virol* 54:817-824; Tarnashiro et al. (1984) *Structure of the heterogeneous L-S junction region of human cytomegalovirus strain AD169 DNA J Virol* 52:541-8; Wagner & Summers (1978) *Structure of the joint region and the termini of the DNA of herpes simplex virus type 1 J Virol* 27:374-87), and has also been observed in HSV amplicons using Southern blot hybridizations (Deiss & Frenkel (1986) *Herpes simplex virus amplicon: cleavage of concatemeric DNA is linked to packaging and involves amplification of the terminally reiterated a sequence J Virol* 57:933-41).

Example 5

CD34$^+$ Cells Isolation and Infection with CMV

Isolation of cord blood CD34$^+$ stem cells was carried out by All Cells Inc. (Berkeley, Calif.) using CD34 Progenitor Cell Isolation Kit (Miltenyi Biotech, Auburn, Calif.). The positive selection of the CD34$^+$ cells was performed using hapten-conjugated antibody to CD34$^+$ followed by anti-hapten antibody coupled to MACS Microbeads. The magnetically labeled cells are enriched on positive selection columns. The purity of the CD34$^+$ population was >95% as analyzed by flow cytometry. The purified CD34$^+$ cells were suspended in Iscove's modified Dulbecco's Minimal Essential Medium containing 5% fetal bovine serum. 2×10$^5$ CD34$^+$ cells were used for each infection with CMV-EGFP amplicon containing stocks, RC2.7EGFP virus, CMV Towne virus, or uninfected cell control. The cells mixed with virus were centrifuged at room temperature for 500×g for 10 mins and were then placed in 37° C. water bath for one hour. The cells were then cultured in 6-well cell culture plates (Costar) for 18-36 hours. At the end of the incubation the cells were harvested for CD34 staining.

Figure 6:
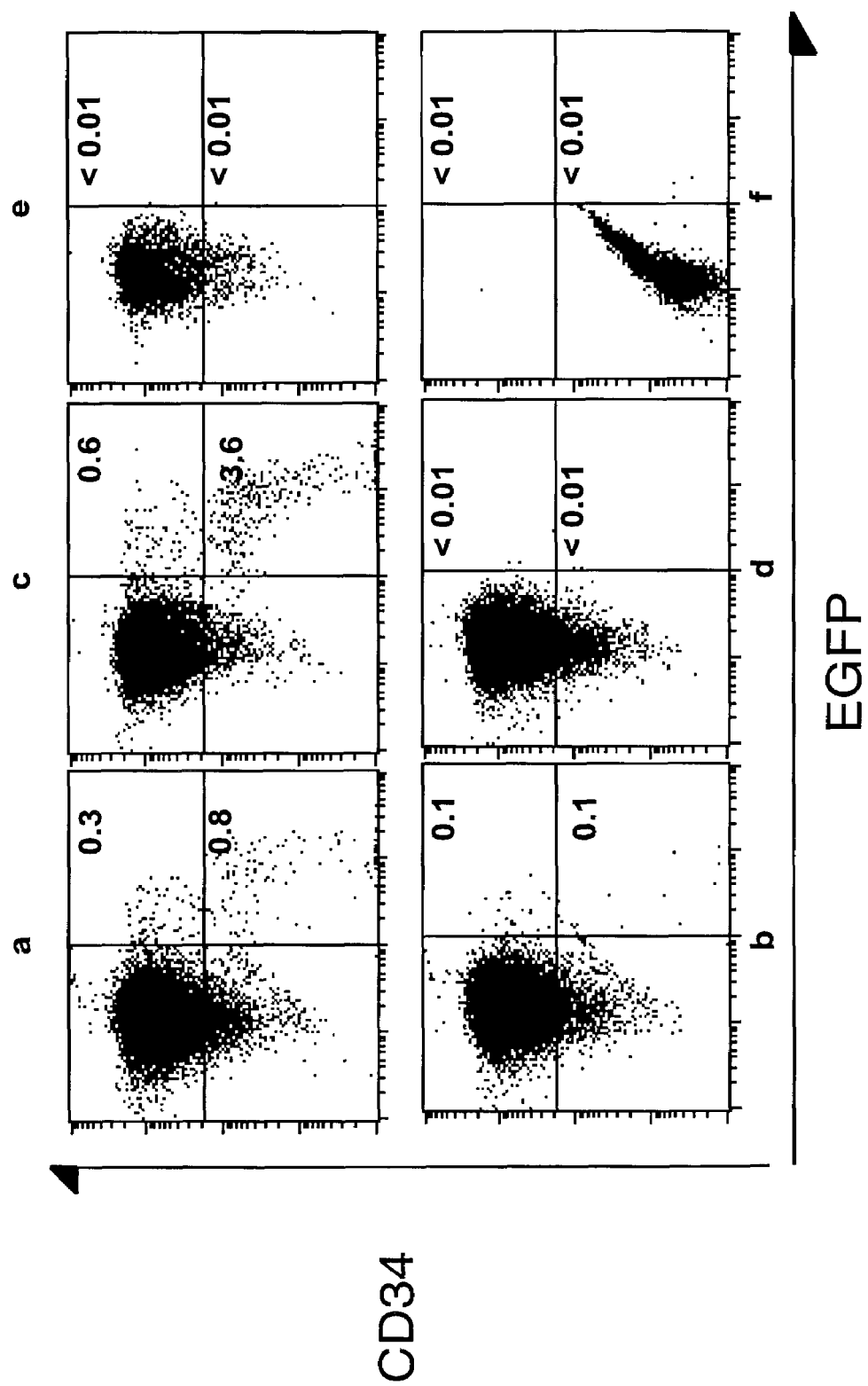
FIG. 6. Flow cytometry analysis of EGFP expression in human cord blood CD34$^+$ cells.

Following infection with the amplicon containing virus particles and helper virus, a loss of primitive cell properties, including a reduction of CD34 expression, was observed, as has previously been reported with respect to cultured CD34$^+$ cells (Gentry & Smith (1999) *Retroviral vector-mediated gene transfer into umbilical cord blood CD34brCD38-CD33- cells Exp Hematol* 27:1244-54; Caux et al. (1989) *Sequential loss of CD34 and class II MHC antigens on purified cord blood hematopoietic progenitors cultured with IL-3: characterization of CD34-, HLA-DR+ cells Blood* 74:1287-94). For example, in experiments with >95% pure cord blood derived CD34$^+$ cell population, a loss of CD34 expression in small percent population (9-12%) of stem cells upon in vitro culture has been observed. EGFP expression was also seen in the CD34- population (FIGS. 6a, 6b, & 6c). It is possible that HCMV infection of CD34 cells induces cell differentiation and loss of primitive properties including reduction of CD34 expression.

Differentiation may be influenced by expression of HLA-related and cytokine-related molecules encoded by HCMV, or induced by HCMV infection (see, e.g., Beck & Barrell (1991) *An HCMV readingframe which has similarity with both the V and C regions of the TCR gamma chain DNA Seq* 2:33-8; Browne et al. (1990) *A complex between the MHC class I homologue encoded by human cytomegalovirus and beta 2 microglobulin Nature* 347:770-2; Gao & Murphy (1994) *Human cytomegalovirus open reading frame US28* encodes a functional beta chemokine receptor *J Biol Chem* 269:28539-42; Lockridge et al. (2000) *Primate cytomegaloviruses encode and express an IL-10-like protein* Virology 268:272-80; Neote et al. (1993) *Molecular cloning, functional expression, and signaling characteristics of a C-C chemokine receptor* Cell 72:415-25; Penfold et al. (1999) *Cytomegalovirus encodes a potent alpha chemokine* Proc Natl Acad Sci USA 96:9839-44; Saederup et al. (1999 Cytomegalovirus-encoded beta chemokine promotes monocyte-associated viremia in the host *Proc Natl Acad Sci USA.* 96:10881-6; Vieira et al. (1998) *Functional analysis of the human cytomegalovirus US28 gene by insertion mutagenesis with the green fluorescent protein gene J Virol* 72:8158-65). The HCMV amplicons contain only the cis-acting ori and packaging sequences, and have no structural gene sequences. However, amplicon containing viral stocks are a mixture with HCMV replication competent helper virus. HCMV induced cell differentiating effect, if any, can be minimized by using a helper virus free amplicon system. A variety of strategies exist for preparing helper virus-free stocks (see, e.g., Fraefel et al. (1996) *Helper virus-free transfer of herpes simplex virus type 1 plasmid vectors into neural cells J Virol* 70:7190-7; Sun et al. (1999) *Improved titers for helper virus-free herpes simplex virus type 1 plasmid vectors by optimization of the packaging protocol and addition of noninfectious herpes simplex virus-related particles (previral DNA replication enveloped particles) to the packaging procedure* Hum Gene Ther 10:2005-11). These preparations are useful for therapeutic applications in immunocompromised patients.

Example 6

Expression of Heterologous Genes in an HCMV Amplicon

Green fluorescent protein (EGFP) under the transcriptional control of the HCMV major immediate early (MIE) promoter was used to demonstrate that the HCMV amplicon vector system supports the expression of a heterologous gene. Two resulting amplicon plasmids, designated Tn9-8GF5 and Tn9-8GF7, both expressed EGFP following transfection of human fibroblast (HF) cells in the absence of helper virus, as expected (not shown). Packaged amplicons were generated by introduction of Tn9-8GFs into HF cells and infecting with HCMV 24 hours later at an m.o.i. of 5 PFU/cell. Transfection-derived viral stocks were passaged onto fresh HF cells supplemented with Towne helper virus at an m.o.i. of 1 PFU/cell. Viral stocks prepared from passage 1 were used to infect HF cells and grown on Lab-Tek 4-well tissue culture chamber slides (Nunc, Inc., Naperville, Ill.). At 72 hours post infection, the slide wells were washed two times with PBS, fixed with cold 4% paraformaldehyde in PBS, washed three times in PBS and mounted with coverslips using Fluoromount. Fluorescing cells were observed with a Carl Zeiss Jena microscope under U illumination. A limited number (approximately 0.01%) of brightly fluorescing cells could be seen by microscopic examination at 72 hours post-infection (data not shown). This demonstrates that a foreign gene can be expressed in the context of a HCMV amplicon viral stock in infected HF cells.

To test the utility of the HCMV amplicon in gene therapy or gene delivery, we used packaged amplicons in viral stocks to infect and deliver an expressed gene into human $CD34^+$ progenitor cells. Amplicon containing viral stocks, expressing enhanced green fluorescent protein (EGFP) (Clonetech, Palo Alto, Calif.), under the control of the major early 2.7 promoter, were produced by cotransfection of plasmid pEAG2.7EGFP with a set of overlapping cosmid clones derived from HCMV Toledo (G. M. Duke, unpublished data). Viral stocks prepared from passage 0 and passage 1 were used to infect $CD34^+$ cells derived from cord blood. At 18 and 36 hours post infection, the cells were stained with anti-CD34 and analyzed for the CD34 marker and EGFP expression. Immunostaining for $CD34^+$ cells was done using Phycoerythrin (PE)-conjugated anti-CD34 antibody (Becton Dickinson, San Jose, Calif.). Infected or control cells were incubated with 20 µl of PE-labeled anti-CD34 antibody for 45 minutes at room temperature and subsequently were washed twice with PBS containing 0.1% BSA. The cells were directly analyzed for EGFP and $CD34^+$ staining on a FACSCalibur instrument (Becton Dickinson, San Jose, Calif.), at 18 and 36 hours post infection.

EGFP expression was observed in $CD34^+$ population in the CMV-EGFP amplicon (0.3%) or the CMV-EGFP virus (0.6%) at 36 hours post infection. FIGS. 6a, 6b, and 6c show flow cytometrric analysis of human cord blood $CD34^+$ cells infected with CMV amplicon containing stocks, virus, or uninfected cell control. CMV-EGFP amplicon (a,b), CMV-EGFP(RC2.7EGFP) virus (c), CMV (Towne) infected (d), or control uninfected human cord blood CD34 cells (e,f), were stained 36 hours post-infection with PE-antiCD34 antibody (a-e), or were left unstained (f), and were analyzed for two-color cytometry analysis using a FACS Calibur instrument.

The dot-plots are generated using Cell Quest software and reveal the $EGFP^+$ cells populations. Numbers in the upper right and lower right quadrants indicate percentage of the $EGFP^+$ $CD34^+$ and $EGFP^+CD34^-$ cells respectively. A frequency lower than 0.01% is considered negative. The uninfected $CD34^+$ cell control or CMV-Towne control virus infected cells were negative for EGFP expression (FIGS. 6d, 6e, and 6f). A small population (7-12%) of the cells lost expression of the $CD34^+$ marker upon in vitro culture. EGFP expression was also observed in a $CD34^-$ population infected with either CMV-EGFP amplicon containing viral stocks (0.8%, 0.1%) or with the CMV-EGFP virus, RC2.7EGFP (3.6%) (FIGS. 6a, 6b, and 6c). The uninfected cell control or CMV Towne infected cells also had a significant CD34 negative population but were negative for EGFP expression (FIGS. 6d, and 6e). At 18 hours post infection the EGFP staining was also observed in $CD34^+$ and $CD34^-$ cells populations (data not shown). These results clearly demonstrate that $CD34^+$ cells can be infected with replication competent or incompetent CMV vectors expressing a foreign gene.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An isolated or recombinant nucleic acid comprising a helper function-dependent viral amplicon, wherein the nucleic acid comprises plasmid Tn9-8 deposited as ATCC Accession Number PTA-9266.

2. The isolated or recombinant nucleic acid of claim 1, further comprising a heterologous polynucleotide.

3. The isolated or recombinant nucleic acid of claim 2, wherein the heterologous polynucleotide encodes a hemoglobin polypeptide.

4. The isolated or recombinant nucleic acid of claim 3, wherein the heterologous polynucleotide is operably linked to a promoter.

5. The isolated or recombinant nucleic acid of claim 4, wherein the promoter comprises an HCMV major immediate early (MIE) promoter.

6. The isolated or recombinant nucleic acid of claim 2, wherein the heterologous polynucleotide encodes at least one anti-retroviral antisense RNA or ribozyme specific for at least one HIV RNA selected from the group consisting of: an HIV tat RNA, an HIV rev RNA, an HIV 5'-LTR RNA, and an HIV gp120 RNA.

7. The isolated or recombinant nucleic acid of claim 6, wherein the heterologous polynucleotide is operably linked to a promoter.

8. The isolated or recombinant nucleic acid of claim 7, wherein the promoter comprises an HCMV major immediate early (MIE) promoter.

9. The isolated or recombinant nucleic acid of claim 2, wherein the heterologous polynucleotide is operably linked to a promoter.

10. The isolated or recombinant nucleic acid of claim 9, wherein the promoter comprises an HCMV major immediate early (MIE) promoter.

11. A helper function-dependent viral amplicon vector system comprising:
   (a) the plasmid Tn9-8 deposited as ATCC Accession Number PTA-9266; and
   (b) a helper virus or one or more nucleic acids encoding one or more helper functions.

12. The vector system of claim 11, wherein the plasmid Tn9-8 deposited as ATCC Accession Number PTA-9266 further comprises a promoter.

13. The vector system of claim 12, wherein the promoter comprises an HCMV major immediate early (MIE) promoter.

14. The vector system of claim 12, wherein the plasmid Tn9-8 further comprises a heterologous polynucleotide operably linked to the promoter.

15. The vector system of claim 14, wherein the heterologous polynucleotide encodes at least one polypeptide.

16. The vector system of claim 15, wherein the heterologous polynucleotide encodes at least one hemaglobin polypeptide.

17. A method of increasing hemaglobin production in a mammalian cell, in vitro, the method comprising:
   (a) culturing a first mammalian cell culture comprising the vector system of claim 16;
   (b) recovering a helper function-dependent infectious viral stock from the cultured first mammalian cell; and
   (c) contacting a second mammalian cell culture in vitro with the helper function-dependent infectious viral stock of step (b);
   thereby producing an infected second mammalian cell culture with increased hemaglobin production.

18. The method of claim 17, wherein the second mammalian cell culture is a hematopoietic stem cell culture.

19. A method of expressing a heterologous polypeptide in a mammalian cell, the method comprising:
   (a) culturing a first mammalian cell culture comprising the vector system of claim 15;
   (b) recovering a helper function-dependent infectious viral stock from the cultured first mammalian cell; and
   (c) contacting a second mammalian cell culture in vitro with the helper function-dependent infectious viral stock of step (b);
   thereby producing an infected second mammalian cell culture expressing a heterologous polypeptide.

20. The vector system of claim 14, wherein the heterologous polynucleotide encodes at least one anti-retroviral antisense RNA or ribozyme specific for at least one HIV RNA selected from the group consisting of: an HIV tat RNA, an HIV rev RNA, an HIV 5'-LTR RNA, and an HIV gp120 RNA.

21. A method of reducing retroviral replication in a mammalian cell, in vitro, the method comprising:
   (a) culturing a first mammalian cell culture comprising the vector system of claim 20;
   (b) recovering a helper function-dependent infectious viral stock from the cultured first mammalian cell; and
   (c) contacting a contacting a second mammalian cell culture in vitro with the helper function-dependent infectious viral stock of step (b);
   thereby producing an infected second mammalian cell culture with reduced retroviral replication.

22. The method of claim 21, wherein the second mammalian cell culture is a cell culture of the hematopoietic lineage.

23. A method of introducing a heterologous polynucleotide into a mammalian cell, the method comprising:
   (a) culturing a first mammalian cell culture comprising the vector system of claim 14;
   (b) recovering a helper function-dependent infectious viral stock from the cultured first mammalian cell; and
   (c) contacting a second mammalian cell culture in vitro with the helper function-dependent infectious viral stock of step (b);
   thereby producing an infected second mammalian cell culture containing a heterologous polynucleotide.

24. A kit comprising the vector system of claim 11 and further comprising instructional materials.

* * * * *